United States Patent
Liu et al.

(10) Patent No.: US 9,453,009 B2
(45) Date of Patent: Sep. 27, 2016

(54) SYNTHESIS OF DEUTERATED MORPHOLINE DERIVATIVES

(71) Applicant: Concert Pharmaceuticals, Inc., Lexington, MA (US)

(72) Inventors: Julie F. Liu, Lexington, MA (US); Xuejun Tang, Ellicott City, MD (US); Scott L. Harbeson, Cambridge, MA (US); Craig E. Masse, Cambridge, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 14/566,244

(22) Filed: Dec. 10, 2014

(65) Prior Publication Data

US 2015/0099714 A1 Apr. 9, 2015

Related U.S. Application Data

(63) Continuation of application No. 13/678,093, filed on Nov. 15, 2012, now abandoned, which is a continuation of application No. 12/456,507, filed on Jun. 17, 2009, now Pat. No. 8,354,557.

(60) Provisional application No. 61/132,284, filed on Jun. 17, 2008.

(51) Int. Cl.
| | |
|---|---|
| *C07D 413/10* | (2006.01) |
| *C07D 295/135* | (2006.01) |
| *C07D 295/033* | (2006.01) |
| *C07C 215/12* | (2006.01) |
| *C07D 295/02* | (2006.01) |
| *C07D 295/06* | (2006.01) |
| *C07D 295/12* | (2006.01) |
| *C07D 413/14* | (2006.01) |
| *C07D 263/06* | (2006.01) |
| *A61K 31/5377* | (2006.01) |
| *A61K 45/06* | (2006.01) |

(52) U.S. Cl.
CPC ......... *C07D 413/10* (2013.01); *A61K 31/5377* (2013.01); *A61K 45/06* (2013.01); *C07C 215/12* (2013.01); *C07D 263/06* (2013.01); *C07D 295/02* (2013.01); *C07D 295/033* (2013.01); *C07D 295/06* (2013.01); *C07D 295/12* (2013.01); *C07D 295/135* (2013.01); *C07D 413/14* (2013.01); *C07B 2200/05* (2013.01)

(58) Field of Classification Search
CPC .................................................. C07D 413/10
See application file for complete search history.

(56) References Cited

U.S. PATENT DOCUMENTS

| | | | |
|---|---|---|---|
| 3,931,177 A | 1/1976 | Coates et al. | |
| 4,914,232 A | 4/1990 | Lai | |
| 5,688,792 A | 11/1997 | Barbachyn et al. | |
| 5,880,118 A | 3/1999 | Barbachyn et al. | |
| 6,221,335 B1 | 4/2001 | Foster | |
| 6,239,152 B1 | 5/2001 | Gordeev et al. | |
| 6,255,304 B1 | 7/2001 | Hester, Jr. et al. | |
| 6,277,985 B1 | 8/2001 | Gadwood et al. | |
| 6,440,710 B1 | 8/2002 | Keinan et al. | |
| 6,603,008 B1 | 8/2003 | Ando et al. | |
| 7,517,990 B2 | 4/2009 | Ito et al. | |
| 7,528,131 B2 | 5/2009 | Persichetti et al. | |
| 7,855,204 B2 | 12/2010 | Tung | |
| 8,354,557 B2 | 1/2013 | Lui et al. | |
| 2005/0004118 A1 | 1/2005 | Jilani | |
| 2005/0038032 A1 | 2/2005 | Allison et al. | |
| 2007/0082929 A1 | 4/2007 | Gant et al. | |
| 2007/0197695 A1 | 8/2007 | Potyen et al. | |
| 2008/0103122 A1 | 5/2008 | Veltri | |
| 2008/0139563 A1* | 6/2008 | Tung et al. | 514/236.8 |
| 2008/0146573 A1 | 6/2008 | Gant et al. | |
| 2009/0093422 A1 | 4/2009 | Tung et al. | |
| 2013/0281456 A1 | 10/2013 | Liu et al. | |

FOREIGN PATENT DOCUMENTS

| | | |
|---|---|---|
| GB | 708523 A | 5/1954 |
| WO | 95/26325 A2 | 10/1995 |
| WO | 97/10223 A1 | 3/1997 |
| WO | 00/05231 A1 | 2/2000 |
| WO | 2007/118651 A1 | 10/2007 |

(Continued)

OTHER PUBLICATIONS

Le Cam ("Cam") Chemica Scripta (1971), 1(2), p. 65-8.*
Baillie, Thomas A., "The Use of Stable Isotopes in Pharmacological Research", Pharmacological Reviews, vol. 33, No. 2, pp. 81-132, 1981.
Browne, Thomas R., "Stable Isotope Techniques in Early Drug Development: An Economic Evaluation", J. Clin. Pharmacol, vol. 38, pp. 213-220, 1998.
Cherrah, et al., "Study of Deuterium Isotope Effects on Protein Binding by Gas Chromatography/Mass Spectrometry. Caffeine and Deuterated Isotopomers", Biomedical and Environmental Mass Spectrometry, vol. 14, pp. 653-657, 1987.
Dyck, et al., "Effects of Deuterium Substitution on the Catabolism of ?-Phenylethylamine: An In Vivo Study", Journal of Neurochemistry, vol. 46, No. 2, pp. 399-404, 1986.

(Continued)

*Primary Examiner* — Yong Chu
(74) *Attorney, Agent, or Firm* — McCarter & English, LLP; Steven G. Davis; Emily Dertz

(57) ABSTRACT

The present invention is directed to a process for preparing a 2,26,6-$d_4$-morpholine derivative represented by Structural Formula (I):

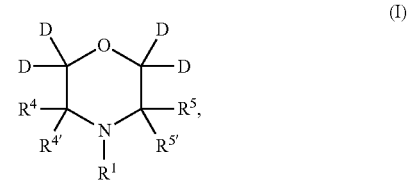

or a salt thereof.

5 Claims, 8 Drawing Sheets

(56) References Cited

FOREIGN PATENT DOCUMENTS

| WO | 2008/070619 A1 | 6/2008 |
|---|---|---|
| WO | 2008/127300 A2 | 10/2008 |

OTHER PUBLICATIONS

Ellermann, et al., "Effect of pentoxifylline on the ischemic rat kidney monitored by 31P NMR spectroscopy in vivo," Biomed. Biochim. Acta, vol. 47, No. 6, pp. 515-521, 1988.

Fisher, et al., "The complexities inherent in attempts to decrease drug clearance by blocking sites of CYP-mediated metabolism," Current Opinion in Drug Discovery & Development, vol. 9, No. 1, pp. 101-109, 2006.

Foster, Allan B., "Deuterium isotope effects in studies of drug metabolism", TIPS, pp. 524-527, 1984.

Foster, Allan B., "Deuterium Isotope Effects in the Metabolism of Drugs and Xenobiotics: Implications for Drug Design", Advances in Drug Research, vol. 14, pp. 2-40, 1985.

Gouyette, et al., "Synthesis of Deuterium-labelled Elliptinium and its Use in Metabolic Studies", Biomedical and Environmental Mass Spectrometry, vol. 15, pp. 243-247, 1988.

Haskins, N.J., "The Application of Stable Isotopes in Biomedical Research", Biomedical Mass Spectrometry, vol. 9, No. 7, pp. 269-277, 1982.

Honma, et al., "Liberation of Deuterium from the Piperidine Ring during Hydroxylation", Drug Metabolism and Disposition, vol. 15, No. 4, pp. 551-559, 1987.

Kushner, et al., "Pharmacological uses and perspectives of heavy water and deuterated compounds", Can. J. Physiol. Pharmacol., vol. 77, pp. 79-88, 1999.

Liu, Youhua, "Epithelial to Mesenchymal Transition in Renal Fibrogenesis: Pathologic Significance, Molecular Mechanism, and Therapeutic Intervention", J. Am. Soc. Nephrol., vol. 15, pp. 1-12, 2004.

Pieniaszek, et al., "Moricizine Bioavailablity via Simultaneous, Dual, Stable Isotope Administration: Bioequivalence Implications", The Journal of Clinical Pharmacology, vol. 39, pp. 817-825, 1999.

Slatter, et al., "Pharmacokinetics, Metabolism, and Excretion of Linezolid following an Oral Dose of [14C]Linezolid to Healthy Human Subjects", Drug Metabolism and Disposition, vol. 29, No. 8, pp. 1136-1145, 2001.

Slatter, et al., "Pharmacokinetics, toxicokinetics, distribution, metabolism and excretion of linezolid in mouse, rat and dog", Xenobiotica, vol. 32, No. 10, pp. 907-924, 2002.

Tonn, et al., "Simultaneous Analysis of Diphenhydramine and a Stable Isotope Analog (2H10)Diphenhydramine Using Capillary Gas Chromatography with Mass Selective Detection in Biological Fluids from Chronically Instrumented Pregnant Ewes", Biological Mass Spectrometry, vol. 22, pp. 633-642, 1993.

Wolen, Robert L., "The Application of Stable Isotopes to Studies of Drug Bioabailablity and Bioequivalence", The Journal of Clinical Pharmacology, vol. 26, pp. 419-424, 1986.

Prescribing information for ZYVOX (Linezoid) Pharmacia & UpJohn Company, Revised Mar. 2007. pp. 1-34.

International Search Report issued in PCT Application No. PCT/US07/22516 on Oct. 16, 2008.

International Search Report—(PCT/US2009/003628) Date of Mailing Nov. 12, 2009.

Adamus, et al., "Synthesis of N,N-dimethylmorpholinium chloride-2-14C", 1982, Journal of Labelled Compounds and Radiopharmaceuticals, vol. 19, pp. 309-312.

Bataille, et al., "Enantioselective synthesis of .alpha.-phenylalkanamines via intermediate addition of Grignard reagents to chiral hydrazones derived from (R)-(−)-2-amino-1-butanol", 1998, Tetrahedron: Asymmetry, vol. 9, pp. 2181-2192.

Cottle, et al., "Preparation of some C-alkylmorpholines", 1946, Journal of Organic Chemistry, vol. 11, pp. 286-291.

Colvin, et al., "Alkylating properties of phosphoramide mustard", 1976, Cancer Research, vol. 36, pp. 1121-1126.

Database CA [Online], Chemical Abstracts Service, Columbus, Ohio, US; Mikula, et al., "Apparatus and methods for preparing morpholine", retrieved from STN Database accession No. 1987:5056.

Database CA [Online], Chemical Abstracts Service, Columbus, Ohio, US; Lindberg, et al., "Mass spectrometry of pethidine and pethidine metabolites. Study utilizing specifically deuterated pethidine", retrieved from STN Database accession No. 1974:504086.

Enders, et al., "(S,S)-3,5-Dimethylmorpholine, a novel C2-symmetric auxiliary. First application in [4+2]-cycloadditions leading to 4-oxohexahydropyridazine derivatives", 1994, Synthesis, vol. 1, pp. 66-72.

Hampton, et al., "New synthesis of morpholine", Journal of the American Chemical Society, 1936, vol. 58, pp. 2338-2339.

Lai, "Hindered amines. Part 6. 3,3,5,5-Tetrasubstituted-2-oxomorpholines and derivatives", Synthesis, 1984, vol. 2, pp. 122-123.

Loeppky, et al., "The synthesis of deuterium-labeled N-nitrosodiethanolamine and N-nitroso-2-hydroxymorpholine", Journal of Labelled Compounds & Radiopharmaceuticals, 1994, vol. 34, pp. 1099-1110.

Loeppky, et al., "Probing the Mechanism of the Carcinogenic Activation of N-Nitrosodiethanolamine with Deuterium Isotope Effects: In Vivo Induction of DNA Single-Strand Breaks and Related in Vitro Assays", Chemical Research in Toxicology, 1998, vol. 11, pp. 1556-1566.

Ludeman, et al., "Oxime Derivatives of the Intermediary Oncostatic Metabolites of Cyclophosphamide and Ifosfamide: Synthesis and Deuterium Labeling for Applications to Metabolite Quantification", Journal of Pharpaceutical Sciences, 1995, vol. 84, pp. 393-398.

Patel, et al., "Metal(IV) phosphates as solid acid catalysts for selective cyclodehydration of 1,n-diols", Green Chemistry, 2001, vol. 3, pp. 143-145.

Jarowicki et al., J Chem. Soc. Perkin. Trans. I, 1998, p. 4005-4037.

Anderson, et al, N-Nitrosodiethanolamine Revisited, Biomedical Mass Spectrometry, 1980; 7(5):205-210.

Cam et al., Chemica Scripta (1971), 1(2):65-68.

\* cited by examiner

1

SYNTHESIS OF DEUTERATED MORPHOLINE DERIVATIVES

RELATED APPLICATION

This application is a continuation application of U.S. patent application Ser. No. 13/678,093, filed Nov. 15, 2012, which is a continuation application of U.S. patent application Ser. No. 12/456,507, filed on Jun. 17, 2009, which claims the benefit of U.S. Provisional Application No. 61/132,284, filed on Jun. 17, 2008. The entire teachings of the above application(s) are incorporated herein by reference.

BACKGROUND OF THE INVENTION

In certain instances, improvements in drug performance have been reported as a result of incorporating deuterium into specific sites of pharmaceutical agents. Site specific incorporation of deuterium with acceptable chemical and isotopic yields can be difficult and expensive to achieve. Therefore, there is need to develop improved processes for making pharmaceutical agents having site-specific deuteration which are economical and have high chemical and isotopic yields.

SUMMARY OF THE INVENTION

The present invention in one embodiment is directed to a novel process for making 2,2,6,6-$d_4$ morpholine derivatives. The process comprises reacting a compound of Formula (II) with an acid to form the compound of Formula (I) or a salt thereof:

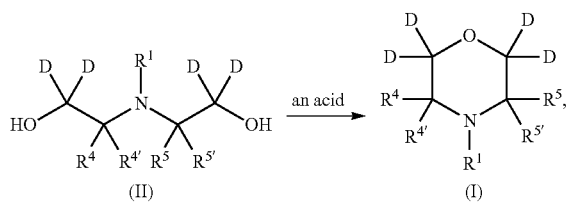

wherein:

$R^1$ is —H, —OH, —NO, —NH$_2$, —NHR$^a$, —N(R$^a$)$_2$, —C(=O)NR$^c$R$^d$, —C(=O)OR$^g$, -phthalimido, —SO$_2$—R$^b$, or a group selected from alkyl, aryl, heteroaryl, aralkyl, heteroaralkyl, cycloalkyl, heterocycloalkyl, cycloalkylalkyl, and heterocycloalkylalkyl wherein the alkyl, aryl, heteroaryl, aralkyl, heteroaralkyl, cycloalkyl, heterocycloalkyl, cycloalkylalkyl, and heterocycloalkylalkyl are each independently optionally substituted with one or more groups selected from halogen, C$_{1-6}$ alkyl, —OR$^e$, —C(=O)OR$^e$, —C(=O)R$^e$, —NO$_2$, —CN, —NH$_2$, —NHR$^a$, —N(R$^a$)$_2$, —NR$^c$C(=O)R$^e$, —C(=O)NR$^c$R$^d$, —S(O)R$^e$, —S(O)$_2$R$^e$, —SR$^e$, and —SO$_2$NR$^c$R$^d$, wherein each C$_{1-6}$ alkyl is optionally substituted with one or more groups selected from halogen, C$_{1-6}$ alkyl, C$_{1-6}$ alkoxy, —OH, C$_{1-6}$ haloalkyl and C$_{1-6}$ haloalkoxy;

each R$^a$ is independently an alkyl optionally substituted with halogen, C$_{1-6}$ alkyl, C$_{1-6}$ alkoxy, —OH, C$_{1-6}$ haloalkyl or C$_{1-6}$ haloalkoxy;

R$^b$ is alkyl, aryl, heteroaryl, aralkyl, or heteroaralkyl, each of which is optionally substituted with one or more groups selected from halogen, C$_{1-6}$ alkyl, —OR$^e$, —C(=O)OR$^e$, —C(=O)R$^e$, —NO$_2$, —CN, —NH$_2$, —NHR$^a$, —N(R$^a$)$_2$, —NR$^c$C(=O)R$^e$, —C(=O)NR$^c$R$^d$, —S(O)R$^e$, —S(O)$_2$R$^e$, —SR$^e$, and —SO$_2$NR$^c$R$^d$, wherein each C$_{1-6}$ alkyl is optionally substituted with one or more groups selected from halogen, C$_{1-6}$ alkyl, C$_{1-6}$ alkoxy, —OH, C$_{1-6}$ haloalkyl and C$_{1-6}$ haloalkoxy;

R$^c$ and R$^d$ are each independently —H or alkyl optionally substituted with one or more groups selected from halogen, C$_{1-6}$ alkyl, —OR$^e$, —C(=O)OR$^e$, —C(=O)R$^e$, —NO$_2$, —CN, —NH$_2$, —NHR$^a$, —N(R$^a$)$_2$, —NR$^c$C(=O)R$^e$, —C(=O)NR$^c$R$^d$, —S(O)R$^e$, —S(O)$_2$R$^e$, —SR$^e$, and —SO$_2$NR$^c$R$^d$, wherein each C$_{1-6}$ alkyl is optionally substituted with one or more groups selected from halogen, C$_{1-6}$ alkyl, C$_{1-6}$ alkoxy, —OH, C$_{1-6}$ haloalkyl and C$_{1-6}$ haloalkoxy;

R$^e$ is —H or alkyl optionally substituted with one or more groups selected from halogen, C$_{1-6}$ alkyl, —OR$^f$, —C(=O)OR$^f$, —C(=O)R$^f$, —NO$_2$, —CN, —NH$_2$, —NHR$^a$, —N(R$^a$)$_2$, —NR$^c$C(=O)R$^f$, —C(=O)NR$^c$R$^d$, —S(O)R$^f$, —S(O)$_2$R$^f$, —SR$^f$, and —SO$_2$NR$^c$R$^d$, wherein each C$_{1-6}$ alkyl substituent is optionally substituted with one or more groups selected from halogen, C$_{1-6}$ alkyl, C$_{1-6}$ alkoxy, —OH, C$_{1-6}$ haloalkyl and C$_{1-6}$ haloalkoxy;

R$^f$ is alkyl, cycloalkyl, heterocycloalkyl, aryl or heteroaryl;

R$^g$ is alkyl optionally substituted with one or more groups selected from halogen, C$_{1-6}$ alkyl, —OR$^f$, —C(=O)OR$^f$, —C(=O)R$^f$, —NO$_2$, —CN, —NH$_2$, —NHR$^a$, —N(R$^a$)$_2$, —NR$^c$C(=O)R$^f$, —C(=O)NR$^c$R$^d$, —S(O)R$^f$, —S(O)$_2$R$^f$, —SR$^f$, and —SO$_2$NR$^c$R$^d$, wherein each C$_{1-6}$ alkyl substituent is optionally substituted with one or more groups selected from halogen, C$_{1-6}$ alkyl, C$_{1-6}$ alkoxy, —OH, C$_{1-6}$ haloalkyl and C$_{1-6}$ haloalkoxy; and R$^4$, R$^{4'}$, R$^5$ and R$^{5'}$ are each independently —H or C$_{1-4}$ alkyl optionally substituted with one or more halogen, C$_{1-6}$ alkyl, C$_{1-6}$ alkoxy, —OH, C$_{1-6}$ haloalkyl, or C$_{1-6}$ haloalkoxy.

In another embodiment, the present invention is directed to a synthetic intermediate for preparing 2,2,6,6-$d_4$ morpholine derivatives. In an example of this embodiment, the present invention is directed to a synthetic intermediate for preparing the deuterated linezolid of compound 10.

(compound 10)

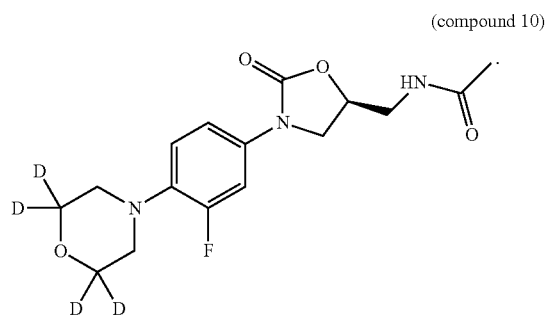

Such intermediates include the compounds of Formulas (I), (Ia), (Ib), and (Ic) and the compounds of Formulas (II), (IIa), and (IIb):

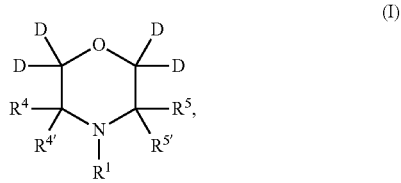

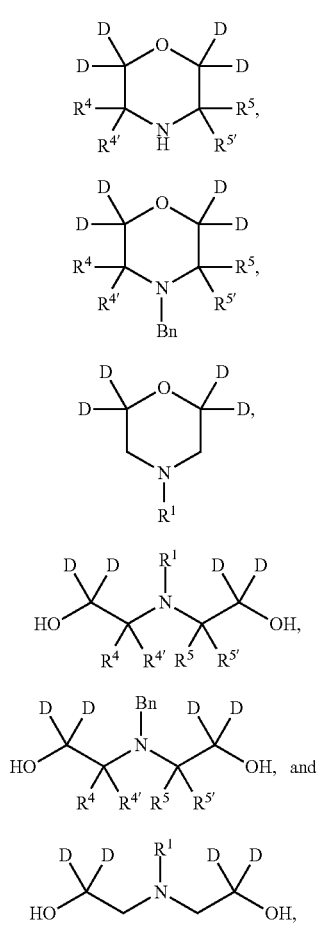

or a salt thereof, wherein each of $R^1$, $R^4$, $R^{4'}$, $R^5$, and $R^{5'}$ are as defined above.

In another embodiment, the present invention is directed to a pharmaceutical composition comprising a pharmaceutically acceptable carrier and the deuterated linezolid of compound 10, or a pharmaceutically acceptable salt thereof, wherein the deuterium enrichment at each position designated as deuterium in compound 10 or a pharmaceutically acceptable salt thereof is at least about 75%.

In another embodiment, the present invention is directed to a method of treating a bacterial infection or a fungal disorder in a subject in need thereof comprising the step of administering to the subject an effective amount of compound 10 or a pharmaceutically acceptable salt thereof, wherein the deuterium enrichment at each position designated as deuterium in compound 10 or a pharmaceutically acceptable salt thereof is at least about 75%.

Another embodiment of the present invention is directed to use of compound 10 or a pharmaceutically acceptable salt thereof for the manufacture of a medicament for treating a bacterial infection or a fungal disorder in a subject in need of the treatment, wherein the deuterium enrichment at each position designated as deuterium in compound 10 or a pharmaceutically acceptable salt thereof is at least about 75%.

Another embodiment of the present invention is directed to compound 10 or a pharmaceutically acceptable salt thereof for use in treating a bacterial infection or a fungal disorder in a subject in need thereof, wherein the deuterium enrichment at each position designated as deuterium in compound 10 or a pharmaceutically acceptable salt thereof is at least about 75%.

BRIEF DESCRIPTION OF THE DRAWINGS

FIG. 1A is a plot showing plasma concentration of linezolid versus time following intravenous administration of linezolid and compound 10 for each male rat tested. FIG. 1B is a plot showing plasma concentration of linezolid versus time following oral administration of linezolid and compound 10 for each male rat tested. FIG. 1C is plot showing mean plasma concentration of linezolid versus time following intravenous and oral administration of linezolid and compound 10. The No. designation in FIGS. 1A and 1B refer to the number given to the test rat.

FIG. 2A is a plot showing plasma concentration of compound 10 versus time following intravenous administration of compound 10 for each male rat tested and linezolid. FIG. 2B is a plot showing plasma concentration of linezolid versus time following oral administration of compound 10 and linezolid for each male rat tested. FIG. 2C is plot showing mean plasma concentration of linezolid versus time following intravenous and oral administration of compound 10 and linezolid. The No. designation in FIGS. 2A and 2B refer to the number given to the test rat.

DETAILED DESCRIPTION OF THE INVENTION

Figure 1A:
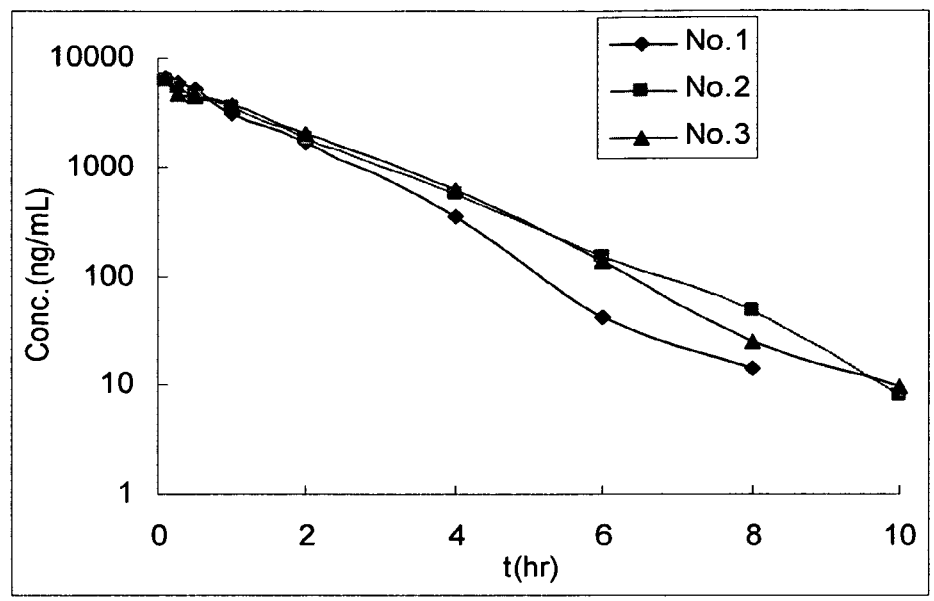
FIGS. 1A-1C depict concentration-time curve of linezolid in male rats following intravenous and oral administration of linezolid in combination with compound 10.

The following definitions are used throughout the specification.

Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3500 times greater than the natural abundance of deuterium, which is 0.015% (i.e., at least 52.5% incorporation of deuterium).

"Halo" or "halogen" means chloro, bromo, or fluoro.

"Alkyl", unless otherwise designated, means an aliphatic hydrocarbon group which may be straight-chain or branched having 1 to 15 carbon atoms. Preferred alkyl groups have 1 to 12 carbon atoms. Even more preferred alkyl groups are $C_{1-6}$ alkyl groups, which are saturated straight-chain or branched hydrocarbons having one to six carbon atoms. A "lower alkyl" group is a $C_{1-4}$ alkyl group. "Branched" means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, heptyl, octyl, nonyl, decyl and dodecyl; preferred are methyl, and i-propyl.

"Aryl" means an aromatic carbocyclic radical containing 6 to 10 carbon atoms. Exemplary aryl groups include phenyl or naphthyl.

"Heteroaryl" means 5-12 membered aromatic monocyclic or multicyclic hydrocarbon ring system in which one or more of the carbon atoms in the ring system is or are element(s) other than carbon, for example nitrogen, oxygen or sulfur. Exemplary heteroaryl groups include pyrazinyl, furanyl, thienyl, pyridyl, pyrimidinyl, isoxazolyl, isothiazolyl, pyridazinyl, 1,2,4-triazinyl, thiadiazolyl, oxadiazolyl, quinolinyl, and isoquinolinyl.

"Aralkyl" means an aryl-alkyl group in which the aryl and alkyl components are as previously described. Preferred aralkyls contain a lower alkyl moiety. Exemplary aralkyl groups include benzyl and 2-phenethyl.

"Heteroaralkyl" means a heteroaryl-alkyl group in which the heteroaryl and alkyl components are as previously described.

"Cycloalkyl" means a non-aromatic mono- or multicyclic ring system of 3 to 10 carbon atoms.

"Heterocycloalkyl" means a non-aromatic mono- or multicyclic hydrocarbon ring system in which at least one of the carbon atoms in the ring system is replaced by a heteroatom, for example nitrogen, oxygen or sulfur. Exemplary heterocycloalkyl groups include pyrrolidinyl, piperidinyl, tetrahydropyranyl, tetrahydrofuranyl, tetrahydrthiopyranyl, and tetrahydrothiofuranyl.

"Cycloalkylalkyl" means a group in which the cycloalkyl and alkyl components are as previously described.

"Heteroycloalkylalkyl" means a group in which the cycloalkyl and alkyl components are as previously described.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

A Brønsted acid is a proton donor. A Lewis acid is an electron pair acceptor. Examples of Brønsted and Lewis acids are well known to the skilled artisan, and are commercially available from a wide variety of sources.

Other definitions are set forth in the table below

| HPLC | High performance liquid chromatography |
| Hr | Hour |
| Kg | Kilogram |

-continued

| LC | Liquid chromatography |
| L | Liter |
| LOQ | Limit of quantitation |
| ug or μg | Microgram |
| mg | Milligram |
| mL | Milliliter |
| Min | Minute |
| MS | Mass spectrometry |
| NA | Not applicable |

The present invention is directed to a process for preparing 2,2,6,6-$d_4$ morpholine derivatives represented by Structural Formula (I):

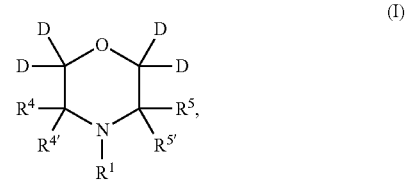

or a salt thereof. Values and specific values for each variable in Structural Formula (I) are provided in the following paragraphs:

$R^1$ is —H, OH, —NO, —NH$_2$, —NHR$^a$, —N(R$^a$)$_2$, —C(=O)NR$^c$R$^d$, —C(=O)OR$^g$, -phthalimido, —SO$_2$—R$^b$, or a group selected from alkyl, aryl, heteroaryl, aralkyl, heteroaralkyl, cycloalkyl, heterocycloalkyl, cycloalkylalkyl, heterocycloalkylalkyl wherein the alkyl, aryl, heteroaryl, aralkyl, heteroaralkyl, cycloalkyl, heterocycloalkyl, cycloalkylalkyl, and heterocycloalkylalkyl are each independently optionally substituted with one or more groups selected from halogen, C$_{1-6}$ alkyl, —OR$^e$, —C(=O)OR$^e$, —C(=O)R$^e$, —NO$_2$, —CN, —NH$_2$, —NHR$^a$, —N(R$^a$)$_2$, —NR$^c$C(=O)R$^e$, —C(=O)NR$^c$R$^d$, —S(O)R$^e$, —S(O)$_2$R$^e$, —SR$^e$, and —SO$_2$NR$^c$R$^d$, wherein each C$_{1-6}$ alkyl is optionally substituted with one or more groups selected from halogen, C$_{1-6}$ alkyl, C$_{1-6}$ alkoxy, —OH, C$_{1-6}$ haloalkyl and C$_{1-6}$ haloalkoxy. In one embodiment, $R^1$ is —H, optionally substituted alkyl, optionally substituted aryl, optionally substituted heteroaryl, optionally substituted aralkyl, —C(=O)NR$^c$R$^d$, —C(=O)OR$^g$, or —SO$_2$—R$^b$. In another embodiment, $R^1$ is —H or optionally substituted benzyl, wherein the benzyl is optionally substituted with one or more groups selected from halogen, —OR$^e$, —C(=O)OR$^e$, —C(=O)R$^e$, —NO$_2$, —CN, —NH$_2$, —NHR$^a$, —N(R$^a$)$_2$, —NR$^c$C(=O)R$^e$, —C(=O)NR$^c$R$^d$, —S(O)R$^e$, —S(O)$_2$R$^e$, —SR$^e$, and —SO$_2$NR$^c$R$^d$. In another embodiment, $R^1$ is —H or unsubstituted benzyl. In another embodiment, $R^1$ is an alkyl group that is optionally substituted with one or more groups selected from halogen, C$_{1-6}$ alkyl, C$_{1-6}$ haloalkyl, —OR$^e$, —C(=O)OR$^e$, —C(=O)R$^e$, —NO$_2$, —CN, —NH$_2$, —NHR$^a$, —N(R$^a$)$_2$, —NR$^c$C(=O)R$^e$, —C(=O)NR$^c$R$^d$, —S(O)R$^e$, —S(O)$_2$R$^e$, —SR$^e$, and —SO$_2$NR$^c$R$^d$, wherein the C$_{1-6}$ alkyl and C$_{1-6}$ haloalkyl substitutents are each further optionally substituted with one or more groups selected from halogen, C$_{1-6}$ alkyl, C$_{1-6}$ alkoxy, —OH, C$_{1-6}$ haloalkyl and C$_{1-6}$ haloalkoxy.

$R^a$, for each occurrence, is independently an alkyl optionally substituted with one or more groups selected from halogen, C$_{1-6}$ alkyl, C$_{1-6}$ alkoxy, —OH, C$_{1-6}$ haloalkyl and C$_{1-6}$ haloalkoxy.

$R^b$ is alkyl, aryl, heteraryl, aralkyl, or heteroaralkyl, each of which is optionally substituted with one or more groups selected from halogen, $C_{1-6}$ alkyl, —$OR^e$, —$C(=O)OR^e$, —$C(=O)R^e$, —$NO_2$, —$CN$, —$NH_2$, —$NHR^a$, —$N(R^a)_2$, —$NR^cC(=O)R^e$, —$C(=O)NR^cR^d$, —$S(O)R^e$, —$S(O)_2R^e$, —$SR^e$, and —$SO_2NR^cR^d$, wherein each $C_{1-6}$ alkyl substitutent is optionally substituted with one or more groups selected from halogen, $C_{1-6}$ alkyl, $C_{1-6}$ alkoxy, —OH, $C_{1-6}$ haloalkyl and $C_{1-6}$ haloalkoxy.

$R^c$ and $R^d$ are each independently —H or an alkyl optionally substituted with one or more groups selected from halogen, $C_{1-6}$ alkyl, —$OR^e$, —$C(=O)OR^e$, —$C(=O)R^e$, —$NO_2$, —$CN$, —$NH_2$, —$NHR^a$, —$N(R^a)_2$, —$NR^cC(=O)R^e$, —$C(=O)NR^cR^d$, —$S(O)R^e$, —$S(O)_2R^e$, —$SR^e$, and —$SO_2NR^cR^d$, wherein each $C_{1-6}$ alkyl substituent is optionally substituted with one or more groups selected from halogen, $C_{1-6}$ alkyl, $C_{1-6}$ alkoxy, —OH, $C_{1-6}$ haloalkyl and $C_{1-6}$ haloalkoxy.

$R^e$ is alkyl optionally substituted with one or more groups selected from halogen, $C_{1-6}$ alkyl, —$OR^f$, —$C(=O)OR^f$, —$C(=O)R^f$, —$NO_2$, —$CN$, —$NH_2$, —$NHR^a$, —$N(R^a)_2$, —$NR^cC(=O)R^f$, —$C(=O)NR^cR^d$, —$S(O)R^f$, —$S(O)_2R^f$, —$SR^f$, and —$SO_2NR^cR^d$, wherein each $C_{1-6}$ alkyl substituent is optionally substituted with one or more groups selected from halogen, $C_{1-6}$ alkyl, $C_{1-6}$ alkoxy, —OH, $C_{1-6}$ haloalkyl and $C_{1-6}$ haloalkoxy;

$R^f$ is alkyl, cycloalkyl, heterocycloalkyl, aryl or heteroaryl;

$R^g$ is —H or alkyl optionally substituted with one or more groups selected from halogen, $C_{1-6}$ alkyl, —$OR^f$, —$C(=O)OR^f$, —$C(=O)R^f$, —$NO_2$, —$CN$, —$NH_2$, —$NHR^a$, —$N(R^a)_2$, —$NR^cC(=O)R^f$, —$C(=O)NR^cR^d$, —$S(O)R^f$, —$S(O)_2R^f$, —$SR^f$, and —$SO_2NR^cR^d$, wherein each $C_{1-6}$ alkyl substituent is optionally substituted with one or more groups selected from halogen, $C_{1-6}$ alkyl, $C_{1-6}$ alkoxy, —OH, $C_{1-6}$ haloalkyl and $C_{1-6}$ haloalkoxy; and $R^4$, $R^{4'}$, $R^5$ and $R^{5'}$ are each independently —H, or $C_{1-4}$ alkyl optionally independently substituted with one or more halogen, $C_{1-6}$ alkyl, $C_{1-6}$ alkoxy, —OH, $C_{1-6}$ haloalkyl or $C_{1-6}$ haloalkoxy.

In one embodiment, $R^e$ is alkyl optionally substituted with one or more groups selected from halogen, $C_{1-6}$ alkyl, —$NO_2$, —$CN$, —$NH_2$, —$NHR^a$, —$N(R^a)_2$, —$C(=O)NR^cR^d$, and —$SO_2NR^cR^d$, wherein each $C_{1-6}$ alkyl substituent is optionally substituted with one or more groups selected from halogen, $C_{1-6}$ alkyl, $C_{1-6}$ alkoxy, —OH, $C_{1-6}$ haloalkyl and $C_{1-6}$ haloalkoxy.

In one embodiment, $R^4$, $R^{4'}$, $R^5$ and $R^{5'}$ are all —H.

In one embodiment, the process of the invention comprises reacting a compound of Formula (II) with an acid to form the compound of Formula (I) or a salt thereof:

(Reaction 1)

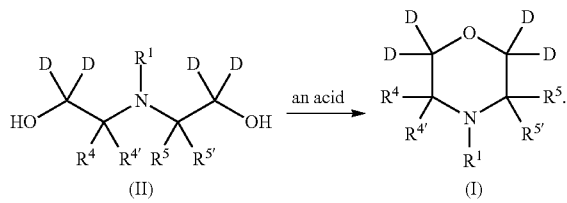

Typically the reaction is performed at a temperature in the range of 100-200° C., such as 120-160° C., such as 140 to 150° C. over a time ranging from 1 to 24 hours, such as between 10 and 18 hours, such as between 16 and 18 hours.

In one embodiment, the compound of Formula (II), or a salt thereof, is prepared by reacting a compound of Formula (III) with a reducing agent:

(Reaction 2)

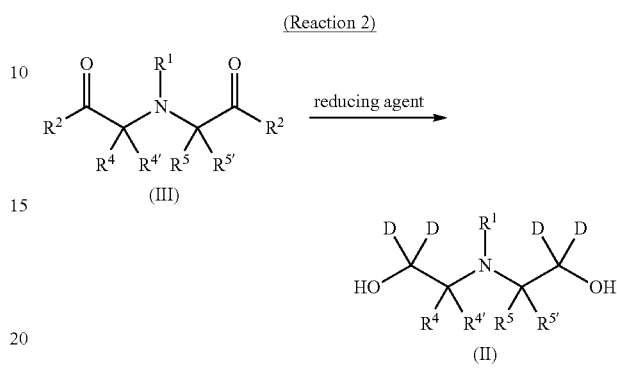

wherein each $R^2$ is D, —OH, or —O(alkyl). For example, $R^2$ may be —OH or —O(alkyl). If $R^2$ is —O(alkyl), the alkyl group in —O(alkyl) is optionally substituted with one or more groups selected from halogen, $C_{1-6}$ alkyl, —$OR^e$, —$C(=O)OR^e$, —$C(=O)R^e$, —$NO_2$, —$CN$, —$NH_2$, —$NHR^a$, —$N(R^a)_2$, —$NR^cC(=O)R^e$, —$C(=O)NR^cR^d$, —$S(O)R^e$, —$S(O)_2R^e$, —$SR^e$, and —$SO_2NR^cR^d$, wherein each $C_{1-6}$ alkyl is optionally substituted with one or more groups selected from halogen, $C_{1-6}$ alkyl, $C_{1-6}$ alkoxy, —OH, $C_{1-6}$ haloalkyl and $C_{1-6}$ haloalkoxy. In one embodiment, $R^2$ is —O($C_{1-3}$ alkyl). In another embodiment, $R^2$ is —OEt (Et=ethyl).

In one embodiment, the process for preparing the compound of Formula (I) comprises:
(a) reacting a compound of Formula (III) with a reducing agent to form the compound of Formula (II); and (b) reacting the compound of Formula (II) with an acid to form the optionally substituted morpholine derivative of Formula (I) or a salt thereof.

In another embodiment, the process described above further comprises the step of removing $R^1$ from a compound of Formula (I) when it is other than —H to form a morpholine derivative of Formula (Ia) or a salt thereof:

(Reaction 3).

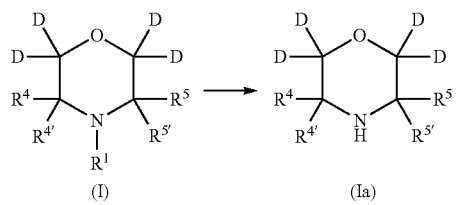

In a specific embodiment, $R^1$ for Reaction 3 is benzyl and the benzyl group is removed under hydrogenation conditions. In one embodiment, reagents for removing $R^1$ from the compound of Formula (I) include hydrogen gas. In one embodiment, hydrogenation may be performed using a metal-based catalyst. More specifically, a palladium-based catalyst or a platinum-based catalyst may be used. Suitable palladium-based catalysts are well-known to one skilled in the art. In one embodiment, the palladium-based catalyst is Pd(OH)$_2$ on carbon. In another embodiment, the catalyst is an elemental palladium catalyst, such as Pd/C, Pd/alumina, or palladium black. A suitable platinum-based catalysts is, for example, an elemental platinum catalyst such as Pt/C.

In one embodiment, for any one of compounds of Structural Formulas (I), (Ia), (II) and (III), $R^4$, $R^{4'}$, $R^5$ and $R^{5'}$ are all —H.

In another embodiment, for any one of compounds of Structural Formulas (I), (II) and (III), $R^1$ is —H, an alkyl optionally substituted as defined above, a benzyl optionally substituted as defined above, —SO$_2$R$^b$, or —C(=O)NR$^c$R$^d$.

In another embodiment, for any one of compounds of Structural Formulas (I), (II) and (III), $R^1$ is —H, an alkyl optionally substituted as defined above, benzyl, or —SO$_2$R$^b$. In another embodiment, $R^1$ is —H, benzyl or —SO$_2$R$^b$. In a more specific embodiment, $R^1$ is benzyl, —SO$_2$-aryl or —SO$_2$-heteroaryl. In an even more specific embodiment, $R^1$ is benzyl. In one aspect of this more specific embodiment, $R^1$ is benzyl; and $R^4$, $R^{4'}$, $R^5$ and $R^{5'}$ are all —H.

Acids that are suitable for Reaction 1 are well known to one skilled in the art. The acid can be a Lewis acid or a Bronsted acid. Examples of suitable acid include, but not limited to, hydrochloric acid, sulfuric acid, phosphoric acid, trifluoroacetic acid, HBF$_4$, ZnCl$_2$ optionally with a co-solvent such as THF, toluenesulfonic acid optionally with a co-solvent such as toluene, and boron trifluoride etherate. In one embodiment, the acid is an aqueous acid. More specifically, the acid is sulfuric acid. Even more specifically, the acid is 70% sulfuric acid.

Suitable reducing agents for Reaction 2 are also well known to one skilled in the art. Some examples of suitable reducing agents include, but are not limited to, diborane-d$_6$ (B$_2$D$_6$), DSiCl$_3$, Et$_3$SiD, diisobutylaluminum deuteride (DIBAL-D), LiAlD$_4$, LiBD$_4$, and NaBD$_4$. In one embodiment, the reducing agent is selected from the group consisting of LiAlD$_4$, LiBD$_4$, and NaBD$_4$. More specifically, the reducing agent is LiAlD$_4$.

The present invention is also directed to the compounds of Formulas (I), (Ia), (Ib), and (Ic) and the synthetic intermediates of Formulas (II), (IIa), and (IIb):

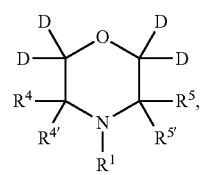
(I)

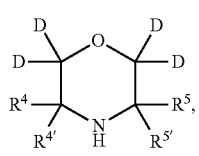
(Ia)

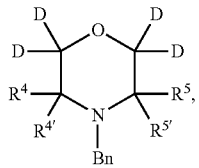
(Ib)

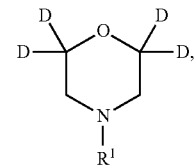
(Ic)

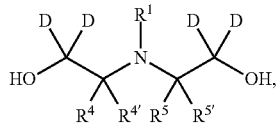
(II)

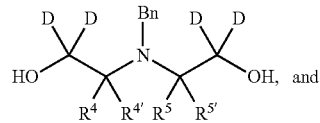
(IIa)

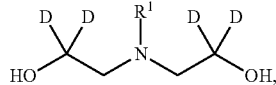
(IIb)

or a salt thereof, wherein each of $R^1$, $R^4$, $R^{4'}$, $R^5$, and $R^{5'}$ are as defined above.

In one embodiment, $R^1$ in any one of Structural Formulas (I), (Ic), (II) and (IIb) is benzyl, —SO$_2$-aryl, or —SO$_2$-heteroaryl, each of which is optionally substituted. In one embodiment, $R^1$ in any one of Structural Formulas (I), (Ic), (II) and (IIb) is —H or benzyl.

As an example, the present invention is directed to compounds 3 and 3a and to synthetic intermediate, compound 2.

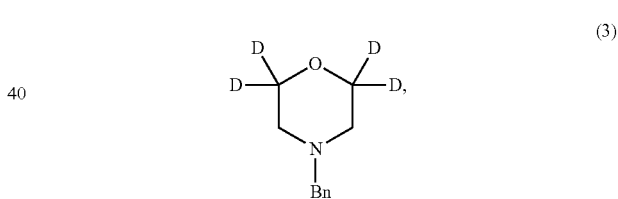
(3)

(3a)

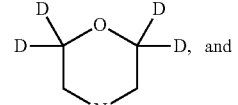
(2)

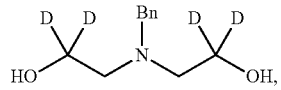

or a salt of any of the foregoing.

The process of the present invention can be used to prepare deuterated version of morpholine-containing pharmaceutical agents. Such pharmaceutical agents include, but are not limited to, xamoterol, xamoterol fumarate, mycophenolate mofetil, rocuronium, rocuronium bromide, moclobemide, landiolol, linezolid, emorfazone, moricizine, moricizine hydrochloride, timolol, timolol maleate, molsidomine, gefitinib, pinaverium, pinaverium bromide, nimorazole, linsidomine, morniflumate, rivaroxaban, aprepitant, fosaprepitant, radafaxine, and pharmaceutical acceptable salts thereof.

As used herein, "morpholine-containing pharmaceutical agents" refers to any pharmaceutical agents that contain one or more morpholine moiety. The morpholine moiety can have one or more substituents on the morpholine ring.

In one embodiment, the process of the present invention can be used to make deuterated linezolid comprising a morpholine moiety represented by the following structural formula:

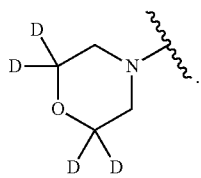

Examples of deuterated linezolid of the present invention are represented by the following structural formulas:

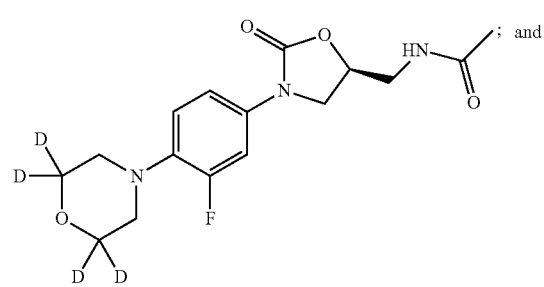

or a pharmaceutically acceptable salt of either of the foregoing.

The deuterated linezolid 10 can be prepared according to Scheme 2 described below.

One embodiment of the present invention is directed to deuterated linezolid 10 and the synthetic intermediates represented by the following structural formulas:

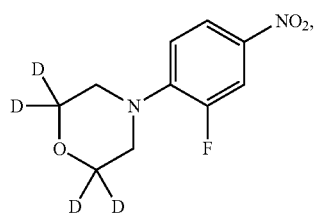

-continued

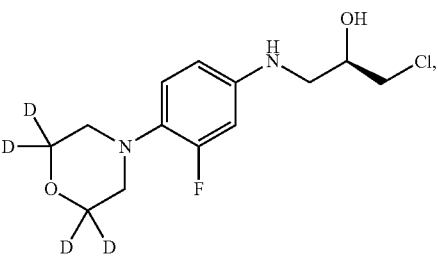

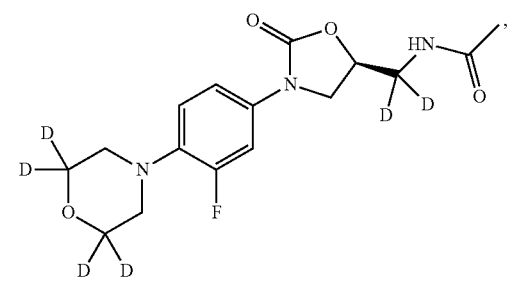

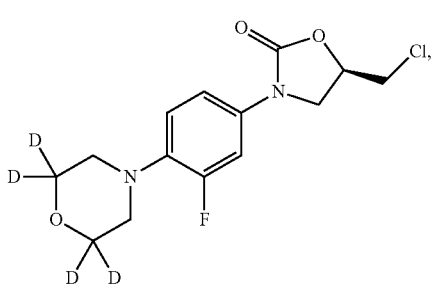

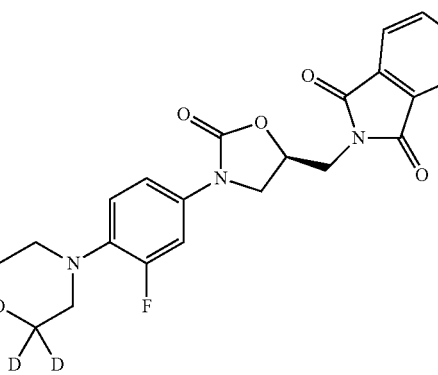

or a salt of any of the foregoing.

In one embodiment, the deuterium enrichment at each position for any one of the compounds represented by Structural Formulas (I)-(Ic), (II)-(IIb), (2), (3), (3a), (4)-(11) is at least about 70%, at least about 75%, at least about 80%, at least about 85%, at least about 90%, at least about 95%, at least about 97%, at least about 97.5%, at least about 99.0% or at least about 99.5%. The percentage for deuterium enrichment refers to mole percentage. When any of these compounds are analyzed by $^1$H NMR, the lack of a visible signal corresponding to the protons alpha to the oxygen indicates deuterium enrichment at those positions of at least 95%.

As used herein, salts include acid salts and base salts. For example, acid salts of a compound of the present invention containing an amine or other basic group can be obtained by reaction of the compound with a suitable organic or inorganic acid resulting in anionic salt. In one embodiment, acid salts of the present invention are pharmaceutically acceptable salts. Such pharmaceutically acceptable salts include, but not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts. Non-pharmaceutically acceptable salts are also included in the present invention, such as trifluoroacetic acid salt.

Salts of the compounds of the present invention containing a carboxylic acid or other acidic functional group can be prepared by reacting with a suitable base. In one embodiment, base salts of the present invention are pharmaceutically acceptable salts. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl) amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

A "pharmaceutically acceptable salt" means any non-toxic salt that, upon administration to a recipient, is capable of providing, either directly or indirectly, a compound of this invention.

In another embodiment, a pharmaceutical composition comprising a deuterated linezolid of the present invention further comprises a second therapeutic agent. The second therapeutic agent includes any compound or therapeutic agent known to have or that demonstrates advantageous properties when administered with an antimicrobial compound, in particular, in anti-microbial therapy, combination therapy with other anti-microbial and/or anti-inflammatory agents is envisaged. Combination therapies according to the present invention thus include the administration of a deuterated linezolid of the present invention (i.e, a deuterated linezolid comprising a 2,2,6,6-d$_4$ morpholinyl moiety and having a deuterium enrichment at each position designated as deuterium of at least about 70%) at least one compound of formula I or Ia, as well as optional use of other anti-microbial agents and optional use of cyclooxygenase inhibitors, particularly selective inhibitors of cyclooxygenase-2. Other anti-microbial therapies and anti-inflammatory agents are described for instance in International Publication Nos. WO 01/34128 and WO 03/061704, which applications are incorporated by reference to the extent that they disclose combinations of anti-microbial and anti-inflammatory therapies.

Examples of second therapeutic agents that may be formulated with a deuterated linezolid of this invention include, but are not limited to, gentamicin, tobramycin, aztreonam, cefazolin, ceftazidime, piperacillin, ciprofloxacin, ofloxacin, levofloxacin, celecoxib, and rofecoxib.

In the pharmaceutical compositions of the invention, the compound of the present invention is present in an effective amount. As used herein, the term "effective amount" refers to an amount which, when administered in a proper dosing regimen, is sufficient to treat (e.g. reduce or ameliorate the severity, duration or progression of the target disorder, prevent the advancement of the target disorder, cause the regression of the target disorder, or enhance or improve the prophylactic or therapeutic effect(s) of another therapy) the target disease or disorder.

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardsley, N.Y., 1970, 537. An effective amount of a compound of this invention can range from about 50 mg to about 2000 mg every 24 hours, if appropriate in the form of several individual doses. In one embodiment the effective amount of a compound of this invention ranges from about 250 mg to about 1250 mg every 24 hours in the form of a single dosage or two separate dosages of about 125 mg to about 625 mg each given every 12 hours. In another embodiment the effective amount of a compound of this invention ranges from about 750 mg to about 1250 mg every 24 hours in the form of a single dosage or two separate dosages of about 375 mg to about 625 mg each given every 12 hours. In still another embodiment the effective amount of a compound of this invention ranges from about 450 mg to about 1200 mg every 24 hours in the form of a single dosage or two separate dosages of about 225 mg to about 625 mg each given every 12 hours. In a more specific embodiment the effective amount of a compound of this invention ranges from about 450 mg to about 750 mg every 24 hours in the form of a single dosage or two separate dosages of about 225 mg to about 375 mg each given every 12 hours. Other ranges of a compound of this invention that fall within or between any of the above-recited ranges are also within the scope of the invention. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

The milligram amounts of compounds present in the pharmaceutical compositions of the present invention and for use in the methods of the present invention represent the amount of free base compound. It will be understood that the use of pharmaceutical salts of the compounds of the present invention will require that the stated amounts be increased so that a mole equivalent of the free base compound is used.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

It is expected that some of the second therapeutic agents referenced above will act synergistically with the compounds of this invention. When this occurs, its will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

According to another embodiment, the invention provides a method of treating a subject suffering from or susceptible to a disease that is beneficially treated by linezolid comprising the step of administering to said subject an effective amount of a deuterated linezolid or a pharmaceutical composition of this invention. Such diseases are well known in the art and include for instance, the treatment or prevention of a variety of disease states typically treated by antimicrobial therapy (e.g., infection, fungal disorders). The deuterated linezolid of this invention, therefore, have utility in the treatment of disorders including those mediated by Gram-positive bacteria and certain Gram-negative and anaerobic bacteria.

In one embodiment, the invention provides a method of treating a subject suffering from or susceptible to an infection caused by a bacteria selected from *Enterococcus faecium, Staphylococcus aureus, Streptococcus agalactiae, Streptococcus pneumoniae, Streptococcus pyrogenes, Enterococcus faecalis, Staphylococcus epidermidis, Staphyloccocus haemolyticus,* and *Pasteurella multocida,*

In another embodiment, the invention provides a method of treating a subject suffering from or susceptible to a disease or disorder (or symptoms thereof) selected from a Gram-positive bacterial infection, Vancomycin-resistant *Enterococcus faecium* infection; nosocomial pneumonia due to *Staphylococcus aureus* and *Streptococcus pneumoniae*; complicated skin and skin structure infections caused by *Staphylococcus aureus, Streptococcus pyogenes,* or *Streptococcus agalactiae*; uncomplicated skin and skin structure infections caused by *Staphylococcus aureus* or *Streptococcus pyogenes*; community-acquired pneumonia caused by *Streptococcus pneumoniae* or *Staphylococcus aureus*; an infection of the eye; and tuberculosis.

In another embodiment, the invention provides a method of treating a subject suffering from diabetic foot infections, nocardiosis, endophthalmitis, keratitis, conjunctivitis, or impetigo.

In another embodiment, the invention provides a method of treating a subject suffering from or susceptible to a disease or disorder (or symptoms thereof) selected from a Gram-positive bacterial infection, Vancomycin-resistant *Enterococcus faecium* infection; nosocomial pneumonia due to *Staphylococcus aureus* and *Streptococcus pneumoniae*; complicated skin and skin structure infections caused by *Staphylococcus aureus, Streptococcus pyogenes,* or *Streptococcus agalactiae*; uncomplicated skin and skin structure infections caused by *Staphylococcus aureus* or *Streptococcus pyogenes*; and community-acquired pneumonia caused by *Streptococcus pneumoniae* or *Staphylococcus aureus*.

In another embodiment, the invention provides a method of treating a patient suffering from or susceptible to a bacterial infection comprising the step of administering to the patient in need thereof over a 24 hour period between about 450 mg and about 750 mg of a deuterated linezolid of this invention. In another embodiment the patient is administered between 450 mg and 700 mg of a deuterated linezolid of the present invention.

In another embodiment, the above method of treatment comprises the further step of co-administering to the patient one or more second therapeutic agents. The choice of second therapeutic agent may be made from any second therapeutic agent known to be useful for co-administration with linezolid.

In a specific embodiment, the combination therapies of this invention include co-administering a deuterated linezolid of the present invention and a second therapeutic agent selected from gentamicin, tobramycin, aztreonam, cefazolin, ceftazidime, piperacillin, ciprofloxacin, ofloxacin, levofloxacin, celecoxib, and rofecoxib.

Example 1

Synthesis of 2,2,6,6-d₄-Morpholine (3a)

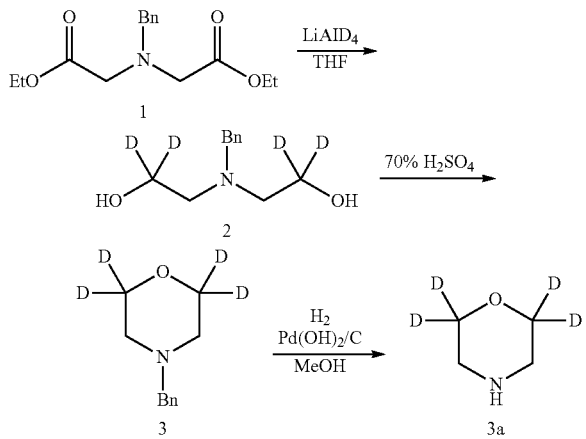

Scheme 1. Preparation of Intermediate 3a.

Step 1. 2,2'-(Benzylazanediyl)bis(1,1-d₂-ethanol) (2). To a solution of diethyl benzyliminodiacetate (1, 55.0 g, 196.9 mmol) in anhydrous tetrahydrofuran (500 mL) at 0° C. was added lithium aluminum deuteride (16.5 g, 393.8 mmol, Cambridge Isotopes, 98 atom % D) in portions with internal temperature below 10° C. After addition the reaction was stirred overnight at room temperature and then quenched sequentially with water (16.5 mL), 15 wt % sodium hydroxide (16.5 mL), and water (49.5 mL) at 0° C. The suspension was stirred 2 hours at room temperature, filtered over celite cake, and washed with THF (400 mL). The filtrate was evaporated in vacuo to give 2 (36.5 g, 93%) as a pale yellow oil.

Step 2. N-benzyl-2,2,6,6-d₄-morpholine (3). A solution of 2 (36.5 g, 183.4 mmol) in 70% sulfuric acid (138 mL) was heated in a sealed tube at 150° C. for 16 hours, cooled to room temperature, and slowly poured onto crushed ice (300 g). The resulting mixture was slowly basified to pH 9 with solid potassium carbonate and mixed with EtOAc (500 mL). The suspension was filtered over a celite cake and washed with EtOAc (400 mL). For the filtrate the two layers were split and the aqueous layer was extracted with EtOAc (2×300 mL). The combined organic layers were dried over sodium sulfate and evaporated in vacuo to give 3 (31.6 g, 95%) as lightly tan oil. The signal corresponding to the protons alpha to the oxygen was not visible in the $^1$H NMR spectrum performed on a Varian Mercury 300 MHz instrument. The absence of the signal indicates that less than 5% of hydrogen is present.

Step 3. 2,2,6,6-$d_4$-Morpholine (3a). A solution of (3, 31.6 g) in methanol (300 mL) was shaken under hydrogen (30 psi) with Pd(OH)$_2$ on carbon (6.3 g) as catalyst until no further hydrogen was consumed. The reaction mixture was filtered over a celite cake and washed with methanol (400 mL). The filtrate was evaporated at 25° C. to give 3a as a pale yellow oil in quantitative yield. The signal corresponding to the protons alpha to the oxygen was not visible in the $^1$H NMR spectrum performed on a Varian Mercury 300 MHz instrument. The absence of the signal indicates that less than 5% of hydrogen is present.

Example 2

Synthesis of (S)—N-((3-(3-Fluoro-4-(2,2,6,6-$d_4$-morpholino)phenyl)-2-oxooxazolidin-5-yl)methyl) acetamide (10)

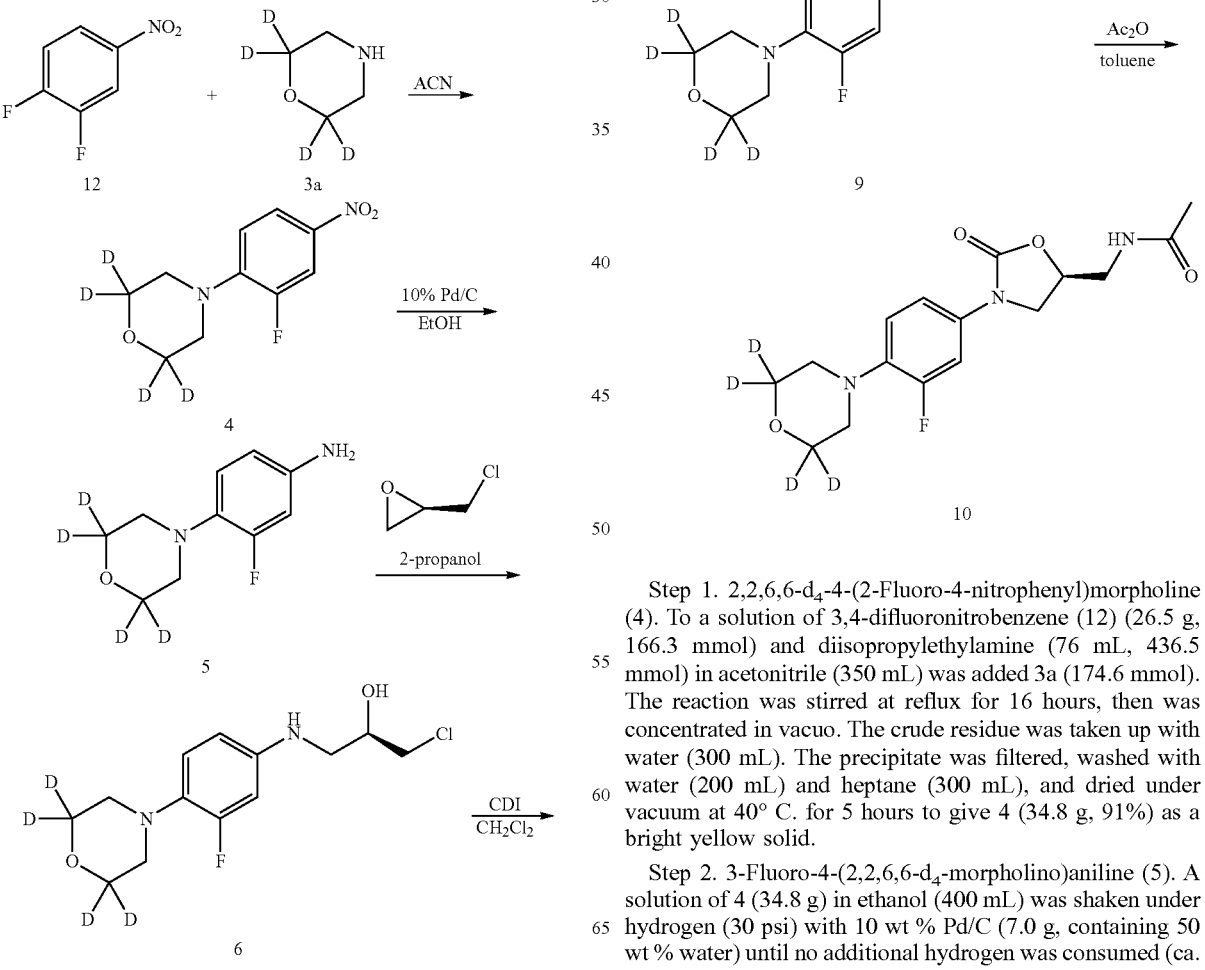

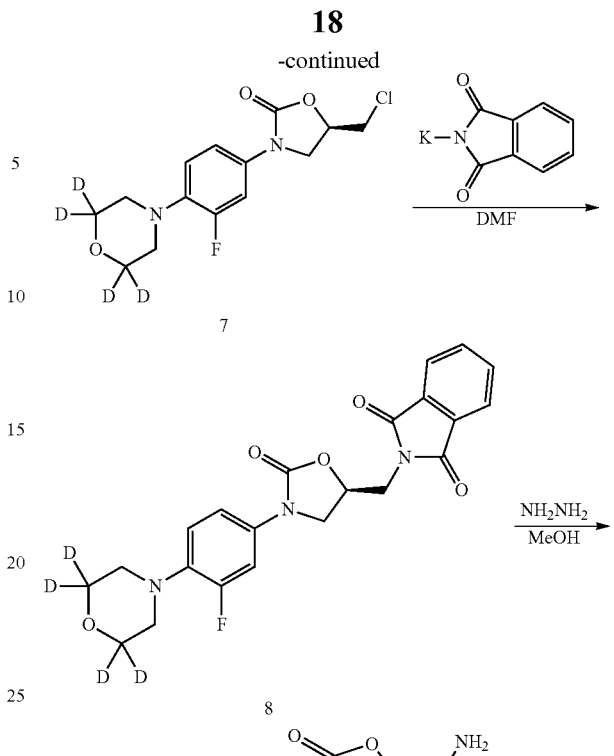

Step 1. 2,2,6,6-$d_4$-4-(2-Fluoro-4-nitrophenyl)morpholine (4). To a solution of 3,4-difluoronitrobenzene (12) (26.5 g, 166.3 mmol) and diisopropylethylamine (76 mL, 436.5 mmol) in acetonitrile (350 mL) was added 3a (174.6 mmol). The reaction was stirred at reflux for 16 hours, then was concentrated in vacuo. The crude residue was taken up with water (300 mL). The precipitate was filtered, washed with water (200 mL) and heptane (300 mL), and dried under vacuum at 40° C. for 5 hours to give 4 (34.8 g, 91%) as a bright yellow solid.

Step 2. 3-Fluoro-4-(2,2,6,6-$d_4$-morpholino)aniline (5). A solution of 4 (34.8 g) in ethanol (400 mL) was shaken under hydrogen (30 psi) with 10 wt % Pd/C (7.0 g, containing 50 wt % water) until no additional hydrogen was consumed (ca. 3 hours). The reaction mixture was filtered over Celite and washed with ethanol (400 mL). The filtrate was concentrated in vacuo to give 5 (26.7 g, 85%) as a white solid.

Step 3. (R)-1-Chloro-3-(3-fluoro-4-(2,2,6,6-$d_4$-morpholino)phenylamino)propan-2-ol (6). To a solution of 5 (2.36 g, 11.8 mmol) in 2-propanol (30 mL) was added (R)-(−)-epichlorohydrin (1.2 g, 13.0 mmol). The reaction was stirred at reflux for 15 hours and another 0.24 g (2.6 mmol) of (R)-(−)-epichlorohydrin was added. The reaction was stirred at reflux another 6 hours and the solvent was removed to give 6 as an oil that was used in the next step without further purification.

Step 4. (R)-5-(Chloromethyl)-3-(3-fluoro-4-(2,2,6,6-$d_4$-morpholino)phenyl)oxazolidin-2-one (7). A solution of 6 (ca. 11.8 mmol) and 1,1'-carbonyldiimidazole (2.68 g, 16.5 mmol) in dichloromethane (100 mL) was stirred overnight at room temperature and concentrated to give a crude oil containing 7.

Step 5. (S)-2-((3-(3-Fluoro-4-(2,2,6,6-$d_4$-morpholino)phenyl)-2-oxooxazolidin-5-yl)methyl)isoindoline-1,3-dione (8). To a solution of 7 (ca. 11.8 mmol) in DMF (50 ml) was added phthalimide potassium salt (2.84 g, 15.3 mmol). The reaction mixture was heated at 100° C. for 6 hours, cooled to room temperature, taken up with water (100 mL), and extracted with MTBE (3×100 mL). The combined organic layers were washed with brine (2×200 mL), dried over sodium sulfate, and concentrated in vacuo. The crude solid was triturated with MTBE (100 mL) to give 8 (3.3 g, 66% for 3 steps) as a white solid.

Step 6. (S)-5-(Aminomethyl)-3-(3-fluoro-4-(2,2,6,6-$d_4$-morpholino)phenyl)oxazolidin-2-one (9). A solution of 8 (3.3 g, 7.68 mmol) and hydrazine monohydrate (2.07 g, 42.3 mmol) in methanol (40 mL) was stirred at reflux for 1 hour. The reaction mixture was concentrated in vacuo, taken up with water (100 mL), and extracted with dichloromethane (3×100 mL). The combine organic layers were washed with water (150 mL), dried over sodium sulfate, and concentrated in vacuo to give 9 (2.16 g) as a tan oil in quantitative yield.

Step 7. (S)—N-((3-(3-Fluoro-4-(2,2,6,6-$d_4$-morpholino)phenyl)-2-oxooxazolidin-5-yl)methyl)acetamide (10). To a solution of 9 (2.16 g, 7.22 mmol) in toluene at room temperature was added acetic anhydride (2 mL, 20.9 mmol). The reaction mixture was warmed at 35° C. for 5 minutes and then stirred overnight at ambient temperature. The reaction mixture was cooled to 0° C., filtered, washed with toluene, and dried at 40° C. for 4 hours to give 10 (1.2 g, 49%) as a white solid. The signal corresponding to the protons alpha to the oxygen is not visible in the $^1$H NMR spectrum.

Example 3

Pharmacokinetic Study in Rats

Materials and Methods 18.08 mg of linezolid and 10.01 mg of compound 10 were dissolved in 10% DMI, 15% Ethanol, 35% PG, and 40% D5W independently to yield a final concentration at 10 mg/mL (pH~6). The combo dose was prepared by mixing both by 1:1 to yield a concentration of 5 mg/mL for each compound (pH~6) for intravenous and oral administration. The obtained solution was clear and colourless. The concentrations of linezolid and compound 10 in each individual dose were confirmed by HPLC method.

Male Sprague Dawley rats (body weight: 170 g to 220 g) were used in this study. Before the pharmacokinetic studies, animals were randomly assigned to the treatment groups. The treatment schedules are shown in Table 1.

TABLE 1

Experimental Design

| No. of Male Rats | Test Article | Test Article Formulation | Dose Route | Target Dose Level (mg/kg) | Target Dose Concentration (mg/mL) | Target Dose Volume (mL/kg) |
|---|---|---|---|---|---|---|
| 3 | linezolid + compound 10 | 10% DMI/15% Ethanol/ 35% PG/40% D5W | IV | 5 mg/kg for each | 5 mg/mL for each | 1 |
| 3 | linezolid + compound 10 | 10% DMI/15% Ethanol/ 35% PG/40% D5W | PO | 5 mg/kg for each | 5 mg/mL for each | 1 |

Blood samples were collected by retro-orbital at 0 (pre-dose) and 0.083, 0.25, 0.5, 1, 2, 4, 6, 8, 10, 12, and 24 hours post-dose. The plasma samples and the dose formulation were stored at −20° C. until bioanalysis.

Sample Analysis

The concentrations of linezolid and compound 10 in plasma were determined using a high performance liquid chromatography/mass spectrometry (HPLC/MS/MS) method.

LC-MS/MS Apparatus

The LC system comprised an Agilent (Agilent Technologies Inc. USA) liquid chromatograph equipped with an isocratic pump (1100 series), an autosampler (1100 series) and a degasser (1100 series). Mass spectrometric analysis was performed using an API3000 (triple-quadrupole) instrument from AB Inc (Canada) with an ESI interface. The data acquisition and control system were created using Analyst 1.4 software from ABI Inc.

Other equipment: XW-80A Vortex mixer (Shanghai); TGL-16B high speed centrifuge (Shanghai), Millipore Academic Ultrapure-water generating system.

Internal Standard (Quetiapine) was a gift from Shanghai Institute of Pharmaceutical Industry. Acetonitrile and methanol (Tedia Inc, USA) were HPLC grade. All other solvents and chemicals were analytical grade or better.

LC-MS/MS Conditions

Chromatographic Conditions

Column: Phenomenex Gemini, C6-pheny, 5 μm, (50 mm×4.6 mm)

Mobile phase: 0.1% Formic acid:Methanol=10:90

Elution rate: 1000 μL/min

Column temperature: 25° C.

Injection volume: 5 μL

Mass
Scan type: Positive MRM
Ion source: Turbo spray Ionization model: ESI
Nebulize gas: 8 L/min Curtain gas: 8 L/min Collision gas: 4 L/min
Ionspray voltage: 4500 v; Temperature: 450° C.
Other parameters:

| Drug name | Q1 | Q3 | Dell time | DP (v) | FP (v) | EP (v) | CE (v) | CXP (v) |
|---|---|---|---|---|---|---|---|---|
| Linezolid | 338.07 | 296.27 | 200 ms | 61 | 160 | 10 | 27 | 20 |
| compound 10 | 342.17 | 300.19 | 200 ms | 56 | 170 | 10 | 27 | 20 |
| Quetiapine | 384.2 | 253.2 | 200 ms | 50 | 200 | 10 | 31 | 15 |

Preparation of Standard Stock Solution

A stock solution of linezolid and compound 10 was prepared by dissolving the drug in methanol to yield a final concentration of 200 μg/mL, respectively. Then proper volume of these two solutions were transferred into one flask, and diluted to the mark with methanol to make a mixture of two compounds with the same concentration of 25 μg/mL. An aliquot of this mixture was diluted using methanol to get a series of working solutions of 25, 50, 250, 500, 2500, 5000, and 25000 ng/mL. Seven calibration standard samples containing 5000, 1000, 500, 100, 50, 10, and 5 ng/mL were obtained by adding 20 μL working solution prepared above into seven Eppendorff tubes containing 100 μL blank plasma. QC samples were prepared by spiking 100 μL blank plasma with 20 μL working solutions of 20000, 4000, and 40 ng/mL to yield final concentration of 4000, 800, and 8 ng/mL.

Stock solution of Quetiapine (internal standard, IS) was prepared by dissolving the drug in methanol to a final concentration of 200 μg/mL. This solution was diluted with methanol to yield a final concentration of 50 ng/mL.

Plasma Sample Process

Plasma samples (0.1 mL) were transferred to Eppendorff tube, then 20 μL methanol, and 300 μL IS solution (50 ng/mL) were added to it. After Vortexing for 1 min and centrifuging for 5 min at 15,000 rpm, 5 μL of supernatant was injected into LC/MS/MS.

Method Validation Results

Specificity

The chromatographic conditions showed that the blank plasma had no interference to the test compounds and IS determination.

Calibration Curve

The analytical curves were constructed using seven non-zero standards ranging from 5 to 5000 ng/mL. A blank sample (matrix sample processed without internal standard) was used to exclude contamination. The linear regression analysis of linezolid and compound 10 were performed by plotting the peak area ratio (y) against the concentration (x) in ng/mL for linezolid or compound 10, respectively. The linearity of the relationship between peak area ratio and concentration were demonstrated by the correlation coefficients (R) obtained for the linear regressions of linezolid and compound 10.

Intra-assay Accuracy

The intra-assay accuracy results (ranged from 83.54% to 106.38% for linezolid, and 94.00% to 113.32% for compound 10) showed that the method is reliable.

Data Analysis

Pharmacokinetic Data Analysis

The concentrations in plasma below the limit of quantitation (LOQ=5 ng/mL) were designated as zero. The pharmacokinetic data analysis was performed using noncompartmental analysis modules in WinNonlin2.0. The bioavailability was calculated as $F(\%)=(Dose_{iv} \times AUC_{oral(0-\infty)})/(Dose_{oral} \times AUC_{iv(0-\infty)})*100\%$.

Results and Discussion

Pharmacokinetics of Linezolid after Combinatory Administration

Figure 1B:
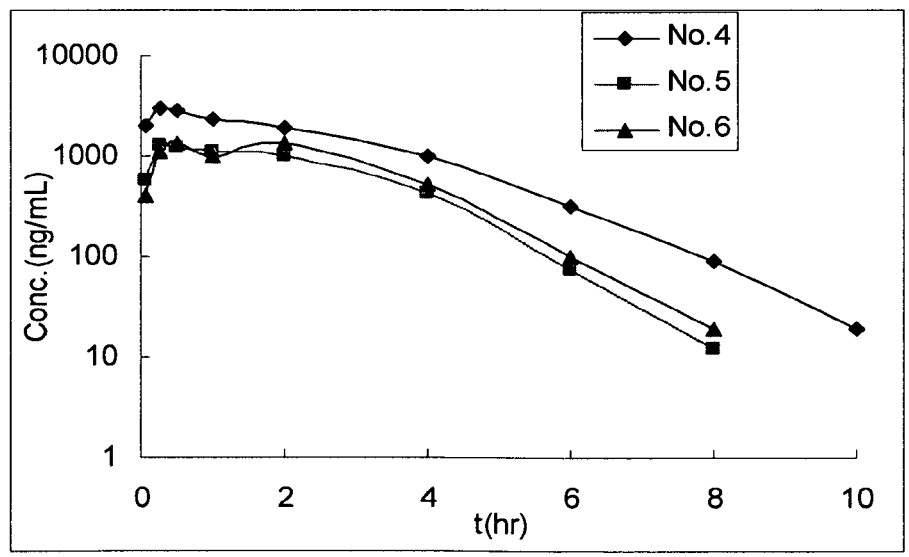
Figure 1C:
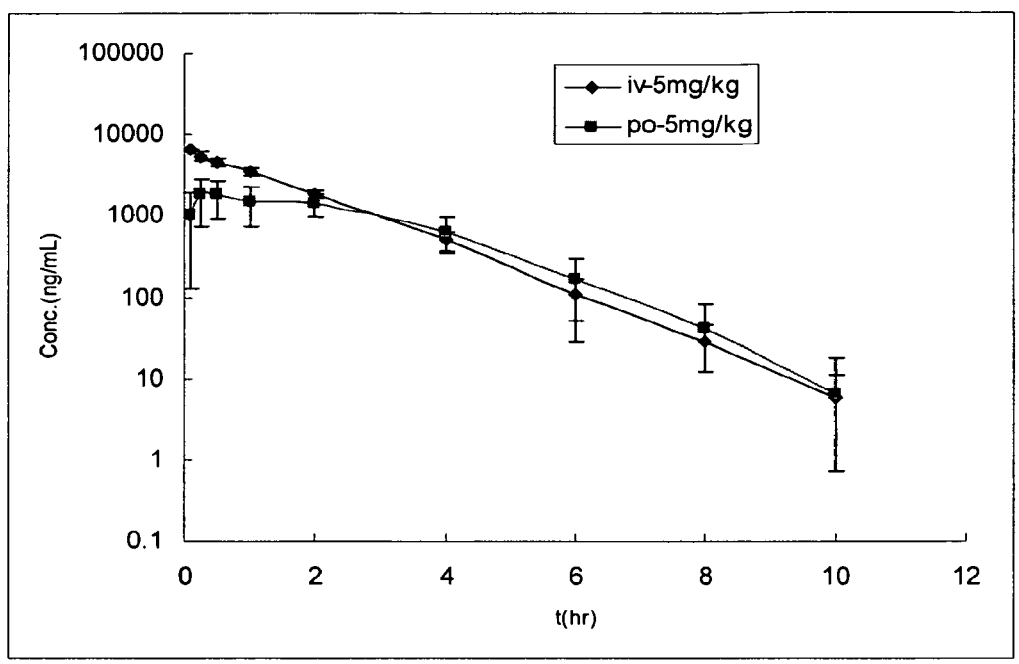

The individual and average concentration-time data of linezolid following intravenous and oral administration linezolid in combination with compound 10 are listed in Table 2 and shown in FIGS. 1A-1C. Selected noncompartmental pharmacokinetic parameters following intravenous and oral dose are listed in Table 3.

TABLE 2

Plasma Concentration of Linezolid in Male Rats Following Intravenous and Oral Administration in Combo with Compound 10

| Time (hr) | Plasma Concentration (ng/mL) | | | | |
|---|---|---|---|---|---|
| IV-5 mg/kg | R7 | R8 | R9 | Mean | SD |
| 0 | BLQ | BLQ | BLQ | NA | NA |
| 0.083 | 6324.03 | 5309.66 | 5983.54 | 5872.41 | 516.24 |
| 0.25 | 4352.05 | 4727.02 | 4742.46 | 4607.18 | 221.08 |
| 0.5 | 3323.69 | 3959.46 | 4045.58 | 3776.24 | 394.28 |
| 1 | 2919.08 | 2636.07 | 2835.48 | 2796.88 | 145.40 |
| 2 | 1361.81 | 1350.43 | 1596.24 | 1436.16 | 138.75 |
| 4 | 278.33 | 320.60 | 361.30 | 320.08 | 41.49 |
| 6 | 58.01 | 61.51 | 69.63 | 63.05 | 5.96 |
| 8 | 15.53 | 26.06 | 16.75 | 19.45 | 5.76 |
| 10 | 4.46 | 7.24 | 7.29 | 6.33 | 1.62 |
| 12 | 0 | 0 | 0 | NA | NA |
| 24 | 0 | 0 | 0 | NA | NA |
| PO-5 mg/kg | R10 | R11 | R12 | Mean | SD |
| 0 | 0 | 0 | 0 | NA | NA |
| 0.083 | 3117.08 | 872.70 | 829.97 | 1606.58 | 1308.30 |
| 0.25 | 3594.56 | 1764.67 | 1099.44 | 2152.89 | 1292.07 |
| 0.5 | 3266.77 | 2142.20 | 1132.83 | 2180.60 | 1067.49 |
| 1 | 2544.56 | 1964.34 | 1169.57 | 1892.82 | 690.28 |
| 2 | 1424.06 | 1728.58 | 860.03 | 1337.56 | 440.69 |
| 4 | 382.80 | 789.74 | 664.96 | 612.50 | 208.48 |
| 6 | 70.20 | 184.51 | 420.25 | 224.99 | 178.50 |
| 8 | 21.39 | 46.16 | 146.45 | 71.33 | 66.22 |
| 10 | 0.00 | 19.47 | 40.28 | 19.92 | 20.14 |
| 12 | 0.00 | 0.00 | 5.15 | 1.72 | 2.97 |
| 24 | 0.00 | 0.00 | 0.00 | NA | NA |

SD: Standard deviation;
NA: Not applicable, or failed to collect samples.

TABLE 3

Selected Pharmacokinetics Parameters of Linezolid in Rats Following
Intravenous and Oral Administration in Combo with Compound 10

|  | $AUC_{(0-t)}$ μg/L*hr | $AUC_{(0-\infty)}$ μg/L*hr | $MRT_{(0-\infty)}$ hr | $T_{1/2z}$ hr | $T_{max}$ hr | $V_z$ L/kg | $CL_z$ L/hr/kg | $C_{max}$ μg/L | F % |
|---|---|---|---|---|---|---|---|---|---|
| IV-5 mg/kg | | | | | | | | | |
| R 1 | 8200.53 | 8207.49 | 1.28 | 1.08 | 0.083 | 0.95 | 0.61 | 6324.03 | |
| R 2 | 8193.82 | 8204.53 | 1.34 | 1.03 | 0.083 | 0.90 | 0.61 | 5309.66 | |
| R 3 | 8956.18 | 8966.61 | 1.36 | 0.99 | 0.083 | 0.80 | 0.56 | 5983.54 | |
| mean | 8450.17 | 8459.54 | 1.33 | 1.03 | 0.083 | 0.88 | 0.59 | 5646.60 | |
| SD | 438.23 | 439.14 | 0.04 | 0.05 | 0 | 0.08 | 0.03 | 476.51 | |
| PO-5 mg/kg | | | | | | | | | |
| R 4 | 7361.11 | 7366.21 | 1.54 | 0.96 | 0.25 | NA | NA | 3594.56 | 87.02 |
| R 5 | 7429.44 | 7434.26 | 2.28 | 1.04 | 0.5 | NA | NA | 2142.20 | 87.82 |
| R 6 | 5474.04 | 5480.19 | 3.17 | 0.83 | 1 | NA | NA | 1169.57 | 64.71 |
| mean | 6754.86 | 6760.22 | 2.33 | 0.94 | 0.58 | NA | NA | 2302.11 | 79.85 |
| SD | 1109.75 | 1109.06 | 0.82 | 0.11 | 0.38 | NA | NA | 1220.38 | 13.12 |

Following an IV combo administration of linezolid and compound 10 at a nominal dose of 5 mg/kg for each, the mean±SD value of systemic clearance for linezolid was 0.59±0.03 L/hr/kg, which corresponded to 17.82% of rat hepatic blood flow (3.31 L/hr/kg). The mean±SD value of half-life ($T_{1/2}$) for linezolid was 1.03±0.05 hr.

Following an IV combo administration of linezolid and compound 10 at a nominal dose of 5 mg/kg for each, the mean±SD values of $C_{max}$ (at 5 minutes after dosing) and $AUC_{(0-\infty)}$ for linezolid was 5646.60±476.51 μg/L and 8459.54±439.14 hr*μg/L. The volume of distribution at terminal phase was 0.88±0.08 L/kg, which corresponded to 131.34% of the total body water (0.67 L/kg) in the rats.

Following an oral combo administration of linezolid and compound 10 at a nominal dose of 5 mg/kg for each, the mean±SD values of $C_{max}$ and $T_{max}$ for inezolid were 2302.11±1220.38 μg/L and 0.58±0.38 hr, respectively; the mean±SD values of $AUC_{(0-\infty)}$ and half-life ($T_{1/2}$) were 6760.22±1109.06 hr*μg/L and 0.94±0.11 hr, respectively. The mean±SD value of bioavailability for inezolid was 79.85±13.12%.

Pharmacokinetics of Compound 10 after Combinatory Administration

Figure 2A:
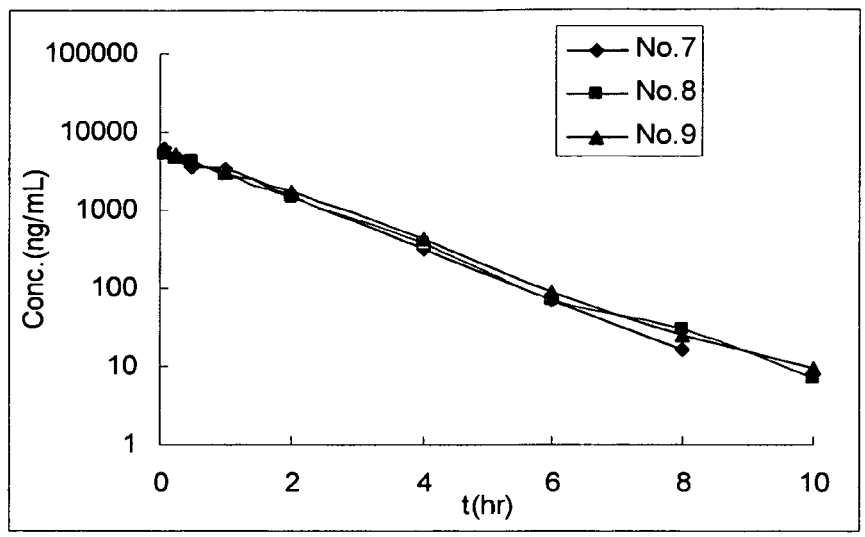
FIGS. 2A-2C depict concentration-time curve of compound 10 in male rats following intravenous and oral administration of compound 10 in combination with linezolid.
Figure 2B:
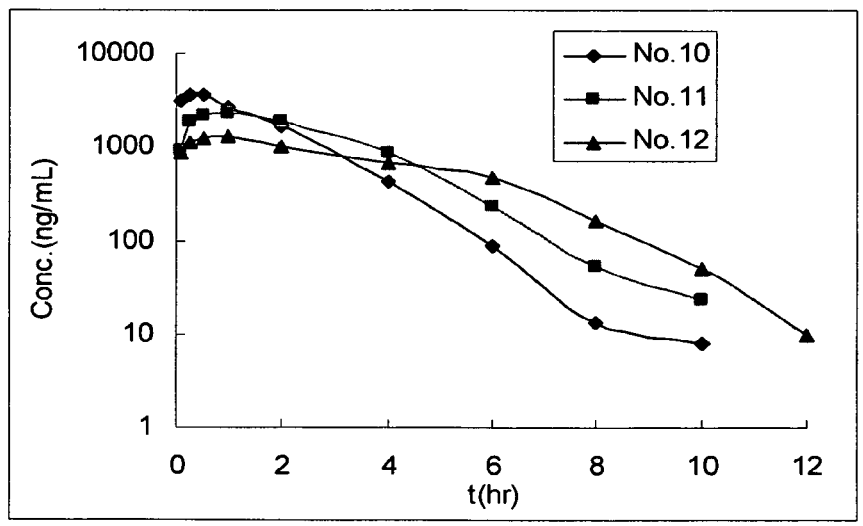
Figure 2C:
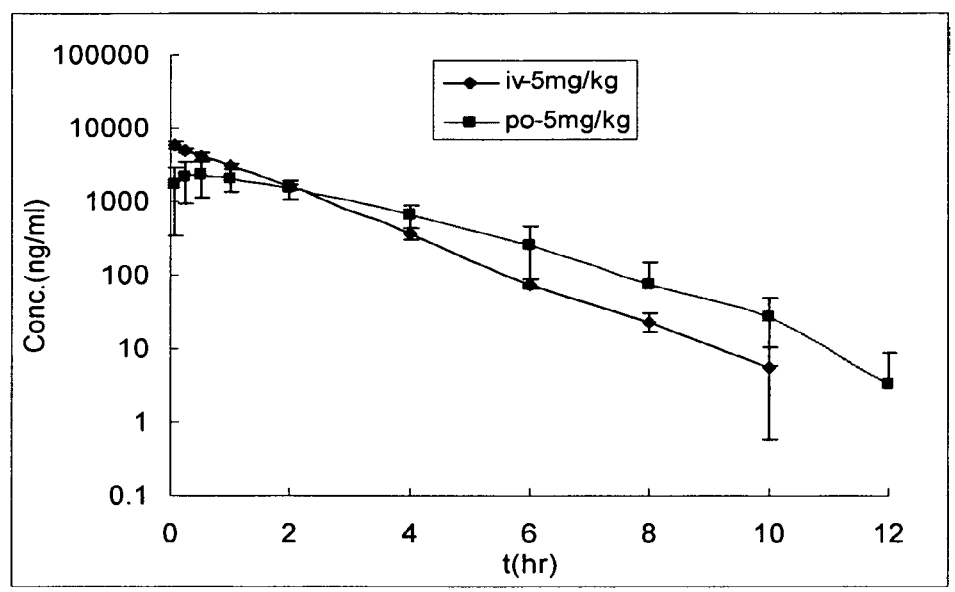

The individual and average concentration-time data of compound 10 following intravenous and oral administration compound 10 in combination with linezolid are listed in Table 4 and shown in FIGS. 2A-2C. Selected noncompartmental pharmacokinetic parameters following intravenous and oral dose are listed in Table 5.

TABLE 4

Plasma Concentration of Compound 10 in Male Rats Following
Intravenous and Oral Administration in Combo with Linezolid

| Time (hr) | Plasma Concentration (ng/mL) | | | | |
|---|---|---|---|---|---|
| IV-5 mg/kg | R7 | R8 | R9 | Mean | SD |
| 0 | BLQ | BLQ | BLQ | NA | NA |
| 0.083 | 6239.85 | 5226.29 | 6160.63 | 5875.59 | 563.70 |
| 0.25 | 4729.24 | 4608.04 | 5155.86 | 4831.05 | 287.75 |
| 0.5 | 3590.16 | 4254.51 | 4412.69 | 4085.79 | 436.45 |
| 1 | 3305.80 | 2745.30 | 2985.25 | 3012.12 | 281.21 |
| 2 | 1517.70 | 1452.58 | 1736.63 | 1568.97 | 148.80 |
| 4 | 319.18 | 368.42 | 438.89 | 375.50 | 60.17 |
| 6 | 70.89 | 70.76 | 88.03 | 76.56 | 9.93 |
| 8 | 15.94 | 29.51 | 25.09 | 23.51 | 6.92 |
| 10 | 0.00 | 7.06 | 9.53 | 5.53 | 4.95 |
| 12 | BLQ | BLQ | BLQ | NA | NA |
| 24 | BLQ | BLQ | BLQ | NA | NA |
| PO-5 mg/kg | R10 | R11 | R12 | Mean | SD |
| 0 | BLQ | BLQ | BLQ | NA | NA |
| 0.083 | 3177.06 | 913.00 | 887.24 | 1659.10 | 1314.65 |
| 0.25 | 3577.65 | 1842.44 | 1122.93 | 2181.01 | 1261.90 |
| 0.5 | 3586.70 | 2137.40 | 1218.21 | 2314.10 | 1194.09 |
| 1 | 2683.05 | 2253.76 | 1281.26 | 2072.69 | 718.22 |
| 2 | 1649.99 | 1843.14 | 1017.10 | 1503.41 | 432.09 |
| 4 | 430.42 | 861.28 | 682.57 | 658.09 | 216.47 |
| 6 | 89.36 | 229.10 | 467.14 | 261.87 | 191.01 |
| 8 | 13.39 | 52.04 | 160.20 | 75.21 | 76.10 |
| 10 | 7.90 | 23.83 | 50.81 | 27.51 | 21.69 |
| 12 | 0.00 | 0.00 | 9.71 | 3.24 | 5.61 |
| 24 | BLQ | BLQ | BLQ | NA | NA |

TABLE 5

Selected Pharmacokinetics Parameters of Linezolid in Rats Following
Intravenous and Oral Administration in Combo with Compound 10

|  | $AUC_{(0-t)}$ μg/L*hr | $AUC_{(0-\infty)}$ μg/L*hr | $MRT_{(0-\infty)}$ hr | $t_{1/2z}$ hr | $T_{max}$ hr | $V_z$ L/kg | $CL_z$ L/hr/kg | $C_{max}$ μg/L | F % |
|---|---|---|---|---|---|---|---|---|---|
| IV-5 mg/kg | | | | | | | | | |
| R 1 | 8978.23 | 8979.14 | 1.30 | 0.83 | 0.083 | 0.67 | 0.56 | 6239.85 | |
| R 2 | 8631.63 | 8634.33 | 1.39 | 1.00 | 0.083 | 0.84 | 0.58 | 5226.29 | |
| R 3 | 9736.59 | 9750.85 | 1.42 | 1.04 | 0.083 | 0.77 | 0.51 | 6160.63 | |
| mean | 9115.48 | 9121.44 | 1.37 | 0.96 | 0.083 | 0.76 | 0.55 | 5693.46 | |
| SD | 565.13 | 571.70 | 0.06 | 0.11 | 0 | 0.09 | 0.04 | 660.68 | |

TABLE 5-continued

Selected Pharmacokinetics Parameters of Linezolid in Rats Following
Intravenous and Oral Administration in Combo with Compound 10

| | $AUC_{(0-t)}$ µg/L*hr | $AUC_{(0-\infty)}$ µg/L*hr | $MRT_{(0-\infty)}$ hr | $t_{1/2z}$ hr | $T_{max}$ hr | $V_z$ L/kg | $CL_z$ L/hr/kg | $C_{max}$ µg/L | F % |
|---|---|---|---|---|---|---|---|---|---|
| | | | | PO-5 mg/kg | | | | | |
| R 4 | 8049.61 | 8061.08 | 1.59 | 1.01 | 0.50 | NA | NA | 3586.70 | 88.25 |
| R 5 | 8090.94 | 8096.42 | 2.32 | 1.05 | 1.00 | NA | NA | 2253.76 | 88.70 |
| R 6 | 6019.61 | 6034.82 | 3.19 | 1.09 | 1.00 | NA | NA | 1281.26 | 65.99 |
| mean | 7386.72 | 6939.38 | 2.37 | 1.05 | 0.83 | NA | NA | 2373.91 | 80.98 |
| SD | 1184.13 | 3365.36 | 0.80 | 0.04 | 0.29 | NA | NA | 1157.41 | 12.98 |

Following an IV combo administration of compound 10 and linezolid at a nominal dose of 5 mg/kg for each, the mean±SD value of systemic clearance for compound 10 was 0.55±0.04 L/hr/kg, which corresponded to 16.62% of rat hepatic blood flow (3.31 L/hr/kg). The mean±SD value of half-life ($T_{1/2}$) for compound 10 was 0.96±0.11 hr.

Following an IV combo administration of compound 10 and linezolid at a nominal dose of 5 mg/kg for each, the mean±SD values of $C_{max}$ (at 5 minutes after dosing) and $AUC_{(0-\infty)}$ for compound 10 was 5693.46±660.68 µg/L and 9121.44±571.70 hr*µg/L. The volume of distribution at terminal phase was 0.76±0.09 L/kg, which corresponded to 113.43% of the total body water (0.67 L/kg) in the rats.

Following an oral combo administration of compound 10 and linezolid at a nominal dose of 5 mg/kg for each, the mean±SD values of $C_{max}$ and $T_{max}$ for compound 10 were 2373.91±1157.41 µg/L and 0.83±0.29 hr, respectively; the mean±SD values of $AUC_{(0-\infty)}$ and half-life ($T_{1/2}$) were 6939.38±3365.36 hr*µg/L and 1.05±0.04 hr, respectively. The mean±SD value of bioavailability for compound 10 was 80.98±12.98%.

CONCLUSIONS

Following combo IV injection of compound 10 with linezolid, the mean values of systemic clearance and half-life for linezolid were 0.59 L/hr/kg and 1.03 hr, respectively; the mean value of $V_z$ was 0.88 L/kg. The mean value of bioavailability after oral administration for linezolid was 79.85%.

Following combo IV injection of compound 10 with linezolid, the mean values of systemic clearance and half-life for compound 10 were 0.55 L/hr/kg and 0.96 hr, respectively; the mean value of $V_z$ was 0.76 L/kg. The mean value of bioavailability after oral administration for compound 10 was 80.98%.

Figure 3:
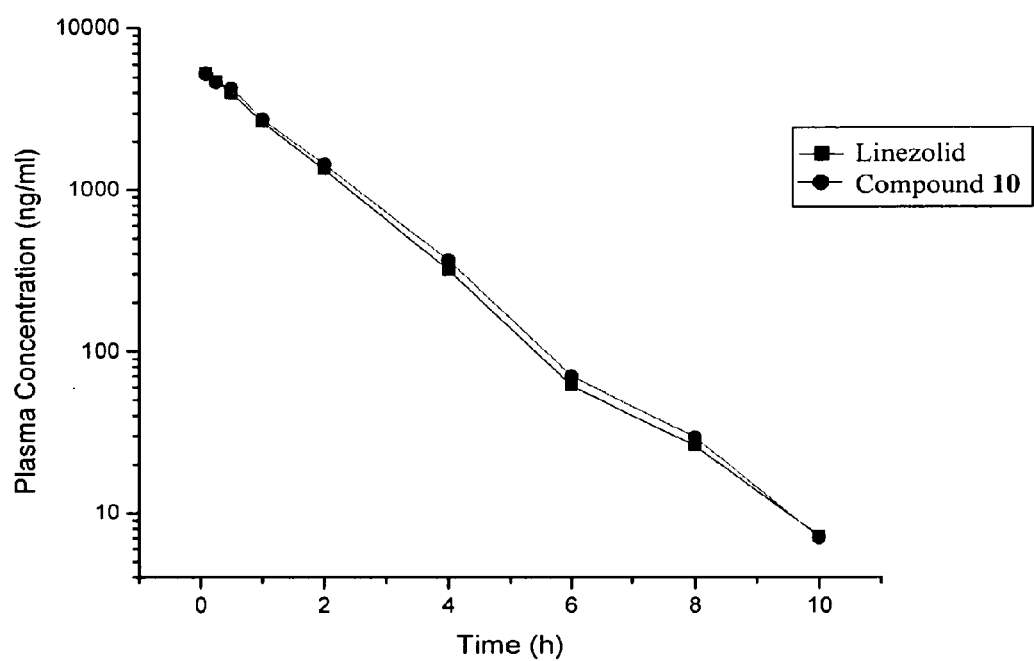
FIG. 3 is a plot showing mean plasma concentration of linezolid (-■-) and compound 10 (-●-) versus time following intravenous administration of linezolid and compound 10.
Figure 4:
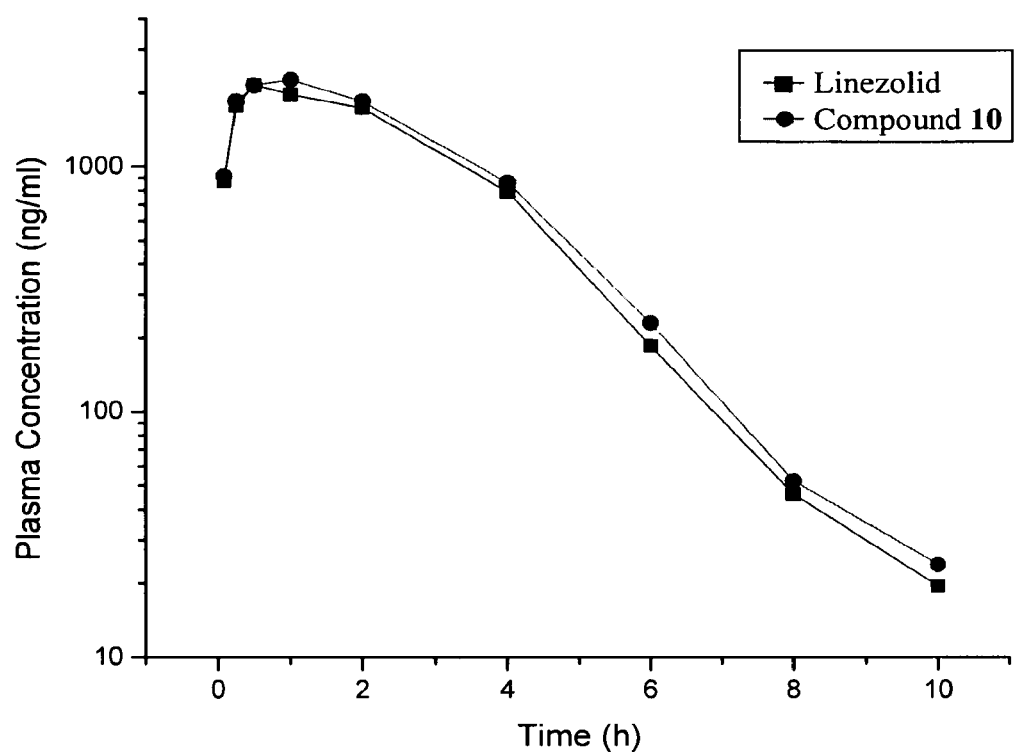
FIG. 4 is a plot showing mean plasma concentration of linezolid (-■-) and compound 10 (-●-) versus time following oral administration of linezolid and compound 10.

A graph showing the mean plasma concentration of linezolid and compound 10 over time following intravenous injection of a combination of linezolid and compound 10 is shown in FIG. 3. A graph showing the mean plasma concentration of linezolid and compound 10 over time following oral administration of a combination of linezolid and compound 10 is shown in FIG. 4.

Example 4

Mitochondria Toxicity Study

HepG2 cells were seeded at 50,000 cells per well in 6-well plates and grown in High-Glucose DMEM in the presence of 6 different concentrations of compound (100 µM, 10 µM, 1 µM, 100 nM, 10 nM and 1 nM). Each concentration was tested in triplicate. Cells were also grown in the corresponding DMSO concentrations present in each of the treatments ($5\times10^{-1}\%$, $5\times10^{-2}\%$, $5\times10^{-3}\%$, $5\times10^{-4}\%$, $5\times10^{-5}\%$, $5\times10^{-6}\%$).

The medium with the compound was changed after 72 hours of treatment and kept for further analysis.

When the cells reached an average of 4 population doublings in the compound, they were trypsinized, centrifuged and washed with phosphate buffered saline. The cells were solubilized in 1.5% laurylmaltoside (in 25 mM Hepes, 100 mM NaCl, pH 7.4), centrifuged at 25,000 g for 20 minutes and supernatants kept for assay.

Enzyme quantity from each well was assessed with duplicate dipsticks. Each dipstick was loaded with 2 µg of solubilized protein to determine the levels of Complex IV (a mtDNA-encoded protein), and Frataxin (a nuclear DNA-encoded protein). Extracts were then stored at −80° C. for further analysis.

The amount of enzymes captured on the dipstick was determined quantitatively with a Hamamatsu Immunochromato Reader. The absorbance signal of two dipsticks measuring enzyme quantity from the same well was averaged (CV<1%) and the means for each triplicate treatment were normalized by interpolation against an assay specific calibration curve.

Figure 5A:
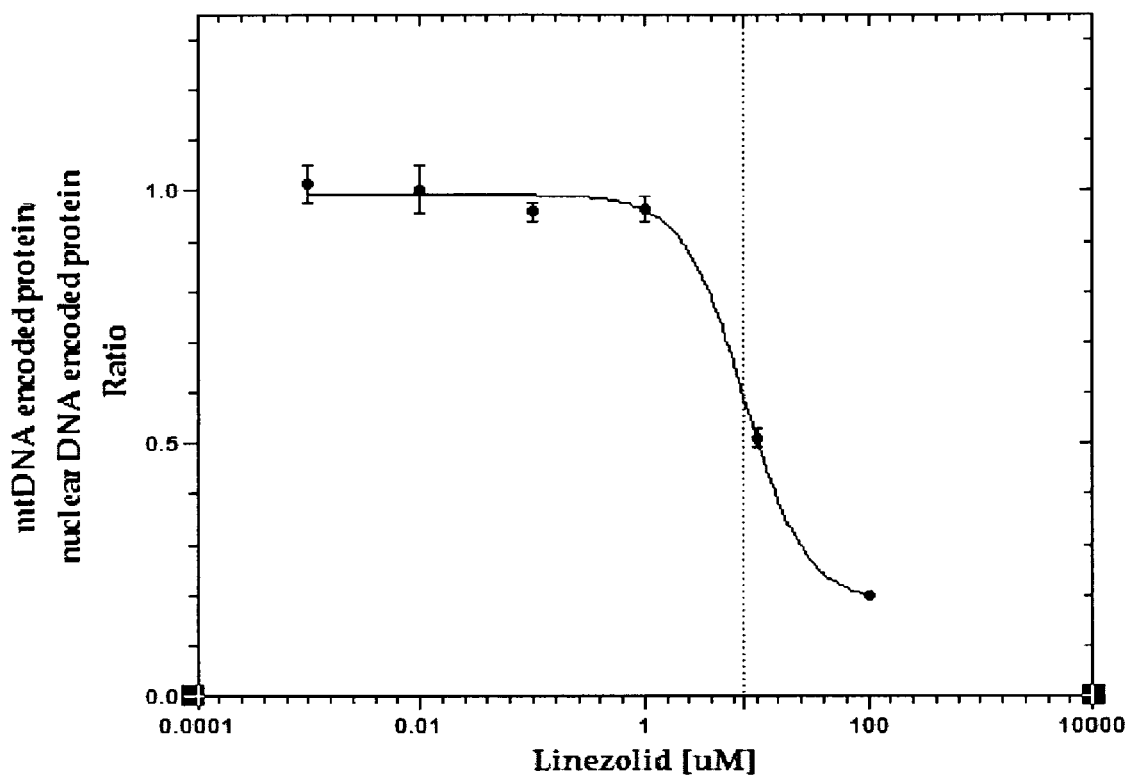
FIGS. 5A and 5B depict inhibition of mtDNA-encoded protein synthesis by linezolid (5A) and compound 10 (5B). The ratio of mtDNA encoded protein over nuclear DNA encoded protein was plotted against the concentration of tested compounds.
Figure 5B:
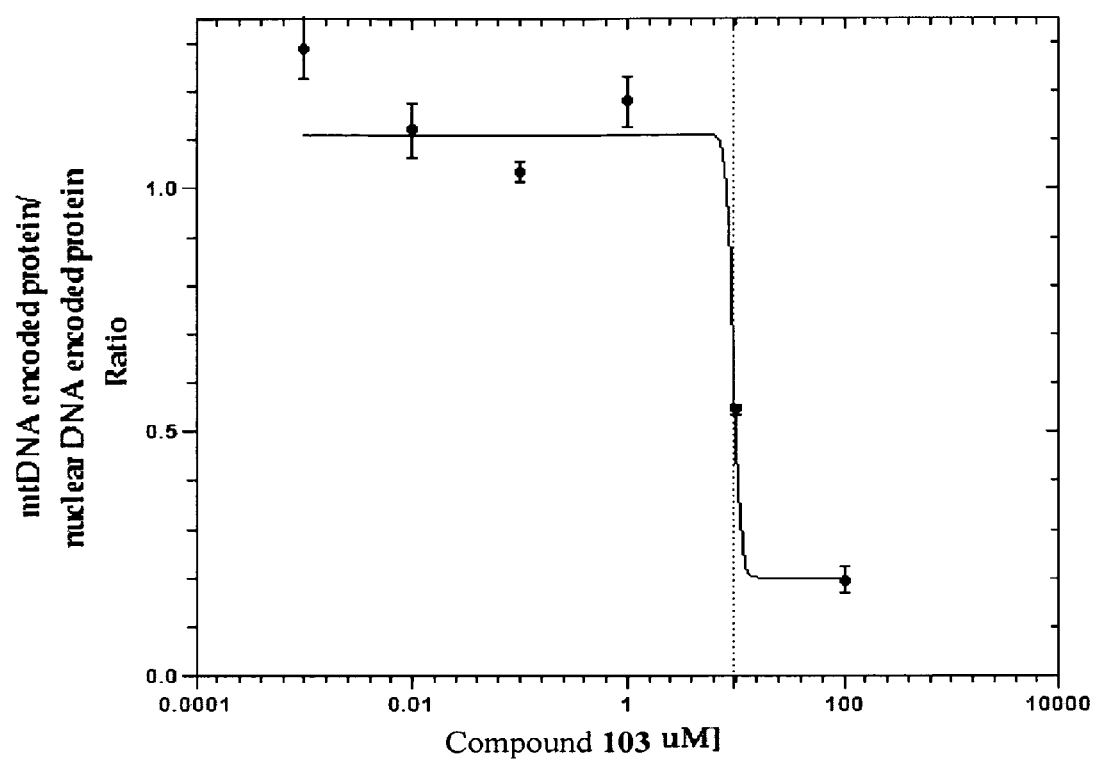

Complex IV/Frataxin Ratios were determined for each triplicate treatment from interpolated values. Triplicate ratios for each treatment concentration were analyzed using a non-linear regression curve in Graph Pad (Log [inhibitor] vs. response–variable slope). Results are shown in FIGS. 5A-5B. $IC_{50}$ values for linezolid and compound 10 are 7.8 and 9.8 µM, respectively.

In conclusion, the mitochondria toxicity for compound 10 is comparable to that of linezolid.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by Formula (I):

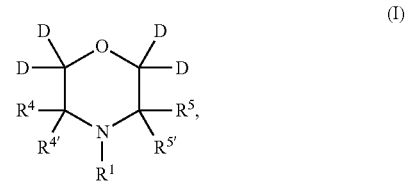

or a salt thereof, wherein
- $R^1$ is —OH, —NO, —NH$_2$, —NHR$^a$, —N(R$^a$)$_2$, —C(=O)NR$^c$R$^d$, —C(=O)OR$^g$, -phthalimido, —SO$_2$—R$^b$, or a group selected from alkyl, heteroaryl, aralkyl, heteroaralkyl, cycloalkyl, heterocycloalkyl, cycloalkylalkyl, heterocycloalkylalkyl, wherein the alkyl, heteroaryl, aralkyl, heteroaralkyl, cycloalkyl, heterocycloalkyl, cycloalkylalkyl, and heterocycloalkylalkyl are each independently optionally substituted with one or more groups selected from halogen, C$_{1-6}$ alkyl, —OR$^e$, —C(=O)OR$^e$, —C(=O)R$^e$, —NO$_2$, —CN, —NH$_2$, —NHR$^a$, —N(R$^a$)$_2$, —NR$^c$C(=O)R$^e$, —C(=O)NR$^c$R$^d$, —S(O)R$^e$, —S(O)$_2$R$^e$, —SR$^e$, and —SO$_2$NR$^c$R$^d$, wherein each C$_{1-6}$ alkyl is optionally substituted with one or more groups selected from halogen, C$_{1-6}$ alkyl, C$_{1-6}$ alkoxy, —OH, C$_{1-6}$ haloalkyl and C$_{1-6}$ haloalkoxy;
- each R$^a$ is independently an alkyl optionally substituted with halogen, C$_{1-6}$ alkyl, C$_{1-6}$ alkoxy, —OH, C$_{1-6}$ haloalkyl or C$_{1-6}$ haloalkoxy;
- R$^b$ is alkyl, aryl, heteroaryl, aralkyl, or heteroaralkyl, each of which is optionally substituted with one or more groups selected from halogen, C$_{1-6}$ alkyl, —OR$^e$, —C(=O)OR$^e$, —C(=O)R$^e$, —NO$_2$, —CN, —NH$_2$, —NHR$^a$, —N(R$^a$)$_2$, —NR$^c$C(=O)R$^e$, —C(=O)NR$^c$R$^d$, —S(O)R$^e$, —S(O)$_2$R$^e$, —SR$^e$, and —SO$_2$NR$^c$R$^d$, wherein each C$_{1-6}$ alkyl is optionally substituted with one or more groups selected from halogen, C$_{1-6}$ alkyl, C$_{1-6}$ alkoxy, —OH, C$_{1-6}$ haloalkyl and C$_{1-6}$ haloalkoxy;
- R$^c$ and R$^d$ are each independently —H or alkyl optionally substituted with one or more groups selected from halogen, C$_{1-6}$ alkyl, —OR$^e$, —C(=O)OR$^e$, —C(=O)R$^e$, —NO$_2$, —CN, —NH$_2$, —NHR$^a$, —N(R$^a$)$_2$, —NR$^c$C(=O)R$^e$, —C(=O)NR$^c$R$^d$, —S(O)R$^e$, —S(O)$_2$R$^e$, —SR$^e$, and —SO$_2$NR$^c$R$^d$, wherein each C$_{1-6}$ alkyl is optionally substituted with one or more groups selected from halogen, C$_{1-6}$ alkyl, C$_{1-6}$ alkoxy, —OH, C$_{1-6}$ haloalkyl and C$_{1-6}$ haloalkoxy;
- R$^e$ is —H or alkyl optionally substituted with one or more groups selected from halogen, C$_{1-6}$ alkyl, —OR$^f$, —C(=O)OR$^f$, —C(=O)R$^f$, —NO$_2$, —CN, —NH$_2$, —NHR$^a$, —N(R$^a$)$_2$, —NR$^c$C(=O)R$^f$, —C(=O)NR$^c$R$^d$, —S(O)R$^f$, —S(O)$_2$R$^f$, —SR$^f$, and —SO$_2$NR$^c$R$^d$, wherein each C$_{1-6}$ alkyl substituent is optionally substituted with one or more groups selected from halogen, C$_{1-6}$ alkyl, C$_{1-6}$ alkoxy, —OH, C$_{1-6}$ haloalkyl and C$_{1-6}$ haloalkoxy;
- R$^f$ is alkyl, cycloalkyl, heterocycloalkyl, aryl or heteroaryl;
- R$^g$ is alkyl optionally substituted with one or more groups selected from halogen, C$_{1-6}$ alkyl, —OR$^f$, —C(=O)OR$^f$, —C(=O)R$^f$, —NO$_2$, —CN, —NH$_2$, —NHR$^a$, —N(R$^a$)$_2$, —NR$^c$C(=O)R$^f$, —C(=O)NR$^c$R$^d$, —S(O)R$^f$, —S(O)$_2$R$^f$, —SR$^f$, and —SO$_2$NR$^c$R$^d$, wherein each C$_{1-6}$ alkyl substituent is optionally substituted with one or more groups selected from halogen, C$_{1-6}$ alkyl, C$_{1-6}$ alkoxy, —OH, C$_{1-6}$ haloalkyl and C$_{1-6}$ haloalkoxy; and
- $R^4$, $R^{4'}$, $R^5$ and $R^{5'}$ are each independently —H or C$_{1-4}$ alkyl optionally substituted with one or more halogen, C$_{1-6}$ alkyl, C$_{1-6}$ alkoxy, —OH, C$_{1-6}$ haloalkyl, or C$_{1-6}$ haloalkoxy;
- and wherein the deuterium enrichment at each position designated as deuterium is at least about 85%.

2. The compound of claim 1, wherein each of $R^4$, $R^{4'}$, $R^5$ and $R^{5'}$ is hydrogen; and wherein the deuterium enrichment at each position designated as deuterium is at least about 95%.

3. The compound of claim 1, wherein $R^1$ is benzyl, —SO$_2$-aryl, or —SO$_2$-heteroaryl.

4. The compound of claim 2, wherein $R^1$ is benzyl.

5. The compound of claim 1, wherein R$^e$ is alkyl optionally substituted with one or more groups selected from halogen, C$_{1-6}$ alkyl, —NO$_2$, —CN, —NH$_2$, —NHR$^a$, —N(R$^a$)$_2$, —C(=O)NR$^c$R$^d$, and —SO$_2$NR$^c$R$^d$, wherein each C$_{1-6}$ alkyl substituent is optionally substituted with one or more groups selected from halogen, C$_{1-6}$ alkyl, C$_{1-6}$ alkoxy, —OH, C$_{1-6}$ haloalkyl and C$_{1-6}$ haloalkoxy.

* * * * *